United States Patent [19]

Hourcade et al.

[11] Patent Number: 5,928,892
[45] Date of Patent: Jul. 27, 1999

[54] MODIFIED COMPLEMENT PROTEASES

[75] Inventors: Dennis E. Hourcade, Wildwood, Mo.; Teresa J. Oglesby, Mobile, Ala.

[73] Assignee: Washington University, St. Louis, Mo.

[21] Appl. No.: 08/687,706

[22] Filed: Jul. 26, 1996

Related U.S. Application Data

[62] Division of application No. 08/177,109, Jan. 3, 1994.

[51] Int. Cl.⁶ .................................................. C12N 15/00
[52] U.S. Cl. ................. 435/69.1; 435/252.3; 435/320.1; 536/23.1; 536/23.5; 530/380
[58] Field of Search ................................ 435/69.1, 252.3, 435/320.1; 536/23.1, 23.5; 530/380

[56] References Cited

FOREIGN PATENT DOCUMENTS 45665 of 1982 European Pat. Off. .

OTHER PUBLICATIONS

Schwaeble et al. (1993) Immunobiol., vol. 188, pp. 221–232.
Schwaeble et al. (1994) EMBL/GenBank/DDBJ Database. Accession No. S67310.
Horiuchi et al. (1993) Molecular Immunology, vol. 30, No. 17, pp. 1587–1592.
Horiuchi et al. (1994) EMBL/GenBank/DDBJ Database. Accession No. S15702.
Mole et al. (1984) J. Biol. Chem. vol. 259, No. 6, pp. 3407–3412.
Mole et al. (1995) EMBL/GenBank/DDBJ Database. Accession No. X72875.
Krych et al. (1991) Proc. Natl. Acad. Sci. USA. vol. 88, pp. 4353–4357.
Krych et al. (1994) J. Biol. Chem. vol. 269, No. 18, pp. 13273–13278.
Perkins et al. (1994) J. Mol. Biol. vol. 238, pp. 104–119.
Almquist et al., "Synthesis and Biological Activity of a Ketomethylene Analogue of a Tripeptide Inhibitor of Angiotensin Converting Enzyme" *J. Med. Chem.* 23:1392–1398 (1980).
Beaucage et al., "Deoxynucleoside Phosphoramidites—A New Class of Key Intermediates for Deoxypolynucleotide Synthesis" *Tetr. Lett.* 22(20):1859–1862 (1981).
Chaiken, "Semisynthetic Peptides and Proteins" *CRC Crit. Rev. Biochem.* 11:255–301 (1981).
Cole et al., "Identification of an additional class of C3–binding membrane proteins of human peripheral blood leukocytes and cell lines" *Proc. Natl. Acad. Sci. USA* 82:859–863 (1985).
Columbatti et al., "The Superfamily of Proteins With von Willebrand Factor Type A–Like Domains: One Theme Common to Components of Extracellular Matrix, Hemostasis, Cellular Adhesion, and Defense Mechanisms" *Blood* 77(11):2305–2315 (1991).
Dykman et al., "Polymorphism of human erythrocyte C3b/C4b receptor" *Prod. Natl. Acad. Sci. USA* 80(6):1698–1702 (1983a).
Dykman et al., "Structural Heterogeneity of the C3b/C4b Receptor (CR1) on Human Peripheral Blood Cells" *J. Exp. Med.* 157(6):2160–2165 (1983b).
Ebenbichler et al., "Human Immunodeficiency Virus Type 1 Activates the Classical Pathway of Complement by Direct C1 Binding through Specific Sites in the Transmembrane Glycoprotein gp41" *J. Exp. Med.* 174:1417–1424 (1991).
Evans et al., "Design of Nonpeptidal Ligands for a Peptide Receptor: Cholecystokinin Antagonists" *J. Med. Chem.* 30:1229–1239 (1987).
Fauchère, "Elements for the Rational Design of Peptide Drugs" *Adv. Drug Res.* 15:29–69 (1986).
Felgner et al., "Lipofection: A highly efficient, lipid–mediated DNA–transfection procedure" *Proc. Natl. Acad. Sci. USA* 84:7413–7417 (1987).
Green et al., "A versatile in vivo and in vitro eukaryotic expression vector for protein engineering" *Nucl. Acids Res.* 16(1):369 (1988).
Hann, "On the Double Bond Isostere of the Peptide Bond: Preparation of an Enkephalin Analogue" *J. Chem. Soc. Perkin Trans. I* 307–314 (1982).
Holladay et al., "Synthesis of Hydroxyethylene and Ketomethylene Dipeptide Isosteres" *Tetrahedron Lett.* 24(41):4401–4404 (1983).
Horiuchi et al., "cDNA Cloning and Expression of Human Complement Component C2" *J. Immunol.* 142(6):2105–2111 (1989).
Horiuchi et al., "Site–Directed Mutagenesis of the Region Around Cys–241 of Complement Component C2: Evidence for a C4b Binding Site" *J. Immunol.* 147(2):584–589 (1991).
Horiuchi et al., "Human Complement Factor B: cDNA Cloning, Nucleotide Sequencing, Phenotypic Conversion by Site–Directed Mutagenesis and Expression" *Molecular Immunology* 30(17):1587–1592 (1993).
Hourcade et al., "The Regulators of Complement Activation (RCA) Gene Cluster" *Adv. Immunology* 45:381–416 (1989).
Hruby, "Conformational Restrictions of Biologically Active Peptides Via Amino Acid Side Chain Groups" *Life Sci.* 31:189–199 (1982).
Hudson et al., "Methionine Enkephalin and Isosteric Analogues" *Int. J. Pept. Prot. Res.* 14:177–185 (1979).
Jennings–White et al., "Synthesis of Ketomethylene Analogs of Dipeptides" *Tetrahedron Lett.* 23(25):2533–2534 (1982).
Kaiser et al., "Peptide and Protein Synthesis by Segment Synthesis–Condensation" *Science* 243:187–191 (1989).

(List continued on next page.)

*Primary Examiner*—Karen Cochrane Carlson
*Assistant Examiner*—Enrique D. Longton
*Attorney, Agent, or Firm*—Arnall Golden & Gregory, LLP

[57] ABSTRACT

Variant complement proteins that are modified in their complement-mediated activity are provided, along with methods for their preparation, and their potential uses. The modifications comprise amino acid substitutions in regions of the complement proteins that contain certain motifs also present in homologous proteins. The amino acid substitutions and their effect on the complement activity of the modified protein are also provided.

22 Claims, 16 Drawing Sheets

OTHER PUBLICATIONS

Kent, "Chemical Synthesis of Peptides and Proteins" *Ann. Rev. Biochem.* 57:957–989 (1988).

Kim et al., "Investigation of Structural Correlates of Factor D Function by Site–Directed Mutagenesis" *Mol. Immunol.* 30:23 (1993).

Krych et al., "Sites within the complement C3b/C4b receptor important for the specificity of ligand binding" *Proc. Natl. Acad. Sci. USA* 88:4353–4357 (1991).

Krych et al., "Analysis of the Functional Domains of Complement Receptor Type 1 (C3b/C4b Receptor; CD35) by Substitution Mutagenesis" *J. Biol. Chem.* 269(18):13273–13278 (1994).

Laemmli, "Cleavage of Structural Proteins during the Assembly of the Head of Bacteriophage T4" *Nature* 227:680–685 (1970).

Luo et al., "Recombinant Human Complement Subcomponent C1s Lacking β–Hydroxyasparagine, Sialic Acid, and One of Its Two Carbohydrate Chains Still Reassembles with C1q and C1r To Form a Functional C1 Complex" *Biochem.* 31:4254–4262 (1992).

Matteucci et al., "Synthesis of Deoxyoligonucleotides on a Polymer Support" *J. Am. Chem. Soc.* 103:3185–3191 (1981).

Mejia et al., "Human Factor B: Complete cDNA sequence of the BF*S allele" *Hum. Immunol.* 39:49–53 (1994).

Merrifield, "Solid Phase Synthesis" *Science* 232:341–347 (1986).

Merrifield, "The Total Synthesis of an Enzyme with Ribonuclease A Activity" *J. Am Chem. Soc.* 91:501–502 (1969).

Michishita et al., "A Novel Divalent Cation–Binding Site in the A Domain of the β2 Integrin CR3 (CD11b/CD18) is Essential for Ligand Binding" *Cell* 72:857–867 (1993).

Mole et al., "Complete Primary Structure for the Zymogen of Human Complement Factor B" *J. Biol. Chem.* 259(6):3407–3412 (1984).

Morley, "Modulation of the action of regulatory peptides by structural modification" *Trends Pharm. Sci.* 463–468 (1980).

Mueckler et al., "The Human Glucose Transporter Can Insert Posttranslationally into Microsomes" *Cell* 44:629–637 (1986).

Müller–Eberhard, "Complement: Chemistry and Pathways" *Inflammation: Basic Principles and Clinical Correlates,* Chapter 3:33–61 (Raven Press, Ltd., New York, 2nd Ed.) (1992).

Mulligan et al., "Protective Effects of Soluble CR1 in Complement– and Neutrophil–Mediated Tissue Injury" *J. Immunology* 148:1479–1485 (1992).

Needleman et al., "A General Method Applicable to the Search for Similarities in the Amino Acid Sequence of Two Proteins" *J. Mol. Biol.* 48:443–453 (1970).

Pearson et al., "Improved tools for biological sequence comparison" *Proc. Natl. Acad. Sci. (U.S.A.)* 85:2444–2448 (1988).

Perkins et al., "A Study of the Structure of Human Complement Component Factor H by Fourier Transform Infrared Spectroscopy and Secondary Structure Averaging Methods" *Biochem.* 27(11):4004–4012 (1988).

Perkins et al., "The Secondary Structure of the von Willebrand Factor Type A Domain in Factor B of Human Complement by Fourier Transform Infrared Spectroscopy: Its Occurrence in Collagen Types VI, VII, XII and XIV, the Integrins and Others Proteins by Averaged Structure Predictions" *J. Mol. Biol.* 238:104–119 (1994).

Pruitt et al., "The Effect of Soluble Complement Receptor Type 1 on Hyperacute Xenograft Rejection" *Transplantation* 52(5):868–873 (1991).

Reid et al., "Structure—function relationships of the complement components" *Immunol. Today* 10(6):177–180 (1989).

*Remington's Pharmaceutical Sciences,* vol. 1, 19th Ed. (Mack Publishing Co., Easton, Pennsylvania, 1995) Table of Contents, emphasis on Chapter 38 "Stability of Pharamaceutical Products", Chapter 56 "Respiratory Drugs", and Chapter 95 "Aerosols".

Rizo et al., "Constrained Peptides: Models of Bioactive Peptides and Protein Substructures" *Ann. Rev. Biochem.* 61:387–418 (1992).

Schwaeble et al., "Human Complement Factor B: Functional Properties of a Recombinant Zymogen of the Alternative Activation Pathway Convertase" *Immunobiol.* 188:221–232 (1993).

Schwaeble et al., "Human Complement Factor B: Functional Properties of a Recombinant Zymogen of the Alternative Activation Pathway Convertase" EMBL/GenBank/DDBJ Database. Accession No. S67310 (1994) (cited in divisional case U.S.S.N. 08/687,706, copy not received with office action, should be the same as disclosed in 1993 paper).

Smith et al., *Adv. Appl. Math.* 2:482 (1981).

Smith et al., "Ultrastructure of Cobra Venom Factor–dependent C3/C5 Convertase and its Zymogen, Factor B of Human Complement" *J. Biol. Chem.* 257(17):9879–9882 (1982).

Spatola et al., "Structure–Activity Relationships of Enkephalins Containing Serially Replaced Thiomethylene Amide Bond Surrogates" *Life Sci.* 38:1243–1249 (1986).

Veber et al., "The design of metabolically–stable peptide analogs" *TINS* pp. 392–396 (1985).

Volanakis, "Participation of C3 and its Ligands in Complement Activation" Current Topics in Microbiol. and Immunol. 153:1–21 (1989) from *The Third Component of Complement Chemistry and Biology* (Springer–Verlag, New York) (1989).

Walter et al., "Preparation of Microsomal Membranes for Cotranslational Protein Translocation" *Meth. Enzymol.* 96:84–93 (1983).

Weisman et al., "Soluble Human complement Receptor Type 1: In Vivo Inhibitor of Complement Suppressing Post–Ischemic Myocardial Inflammation and Necrosis" *Science* 249:146–151 (1990).

Yeh et al., "Recombinant Soluble Human Complement Receptor Type 1 Inhibits Inflammation in the Reversed Passive Arthus Reaction in Ratsf" *J. Immunology* 146(1):250–256 (1991).

```
         10         20         30         40
1234567890 1234567890 1234567890 1234567890
TGACCAGGTC TAGGTCTGGA GTTTCAGCTT GGACACTGAG    40

CCAAGCAGAC AAGCAAAGCA AGCCAGGACA CACCATCCTG    80

CCCCAGGCCC AGCTTCTCTC CTGCCTTCCA ACGCCATGGG   120
                                     MetGl

GAGCAATCTC AGCCCCCAAC TCTGCCTGAT GCCCTTTATC   160
ySerAsnLeu SerProGlnL euCysLeuMe tProPheIle

TTTGGGCCTCT TGTCTGGAGG TGTGACCACC ACTCCATGGT  200
LeuGlyLeuL euSerGlyGl yValThrThr ThrProTrpS

CTTTGGCCCA GCCCCAGGGA TCCTGCTCTC TGGAGGGGGT   240
erLeuAlaGl nProGlnGly SerCysSerL euGluGlyVa

AGAGATCAAA GGCGGCTCCT TCCGACTTCT CCAAGAGGGC   280
lGluIleLys GlyGlySerP heArgLeuLe uGlnGluGly

CAGGCACTGG AGTACGTGTG TCCTTCTGGC TTCTACCCGT   320
GlnAlaLeuG luTyrValCy sProSerGly PheTyrProT
```

ACCCTGTGCA  GACACGTACC  TGCAGATCTA  CGGGGTCCTG     360
yrProValGl  nThrArgThr  CysArgSerT  hrGlySerTr

GAGCACCCTG  AAGACTCAAG  ACCAAAAGAC  TGTCAGGAAG     400
pSerThrLeu  LysThrGlnA  spGlnLysTh  rValArgLys

GCAGAGTGCA  GAGCAATCCA  CTGTCCAAGA  CCACACGACT     440
AlaGluCysA  rgAlaIleHi  sCysProArg  ProHisAspP

TCGAGAACGG  GGAATACTGG  CCCCGGTCTC  CCTACTACAA     480
heGluAsnGl  yGluTyrTrp  ProArgSerP  roTyrTyrAs

TGTGAGTGAT  GAGATCTCTT  TCCACTGCTA  TGACGGTTAC     520
nValSerAsp  GluIleSerP  heHisCysTy  rAspGlyTyr

ACTCTCCGGG  GCTCTGCCAA  TCGCACCTGC  CAAGTGAATG     560
ThrLeuArgG  lySerAlaAs  nArgThrCys  GlnValAsnG

GCCGGTGGAG  TGGGCAGACA  GCGATCTGTG  ACAACGGAGC     600
lyArgTrpSe  rGlyGlnThr  AlaIleCysA  spAsnGlyAl
```

GGGGTACTGC TCCAACCCGG GCATCCCCAT TGGCACAAGG          640
aGlyTyrCys SerAsnProG lyIleProIl eGlyThrArg

AAGGTGGGCA GCCAGTACCG CCTTGAAGAC AGCGTCACCT          680
LysValGlyS erGlnTyrAr gLeuGluAsp SerValThrT

ACCACTGCAG CCGGGGGCTT ACCCTGCGTG GCTCCCAGCG          720
yrHisCysSe rArgGlyLeu ThrLeuArgG lySerGlnAr

GCGAACGTGT CAGGAAGGTG GCTCTTGGAG CGGGACGGAG          760
gArgThrCys GlnGluGlyG lySerTrpSe rGlyThrGlu

CCTTCCCTGCC AAGACTCCTT CATGTATGAC ACCCCTCAAG         800
ProSerCysG lnAspSerPh eMetTyrAsp ThrProGlnG

AGGTGGCCGA AGCTTTCCTG TCTTCCCTGA CAGAGACCAT          840
luValAlaGl uAlaPheLeu SerSerLeuT hrGluThrIl

AGAAGGAGTC GATGCTGAGG ATGGGCACGG CCCAGGGGAA          880
eGluGlyVal AspAlaGluA spGlyHisGl yProGlyGlu
```

CAACAGAAGC GGAAGATCGT CCTGGACCCT TCAGGCTCCA  920
GlnGlnLysA rgLysIleVa lLeuAspPro SerGlySerM

TGAACATCTA CCTGGTGCTA GATGGATCAG ACAGCATTGG  960
etAsnIleTy rLeuValLeu AspGlySerA spSerIleGl

GGCCAGCAAC TTCACAGGAG CCAAAAAGTG TCTAGTCAAC 1000
yAlaSerAsn PheThrGlyA laLysLysCy sLeuValAsn

TTAATTGAGA AGGTGGCAAG TTATGGTGTG AAGCCAAGAT 1040
LeuIleGluL ysValAlaSe rTyrGlyVal LysProArgT

ATGGTCTAGT GACATATGCC ACATACCCCA AAATTTGGGT 1080
yrGlyLeuVa lThrTyrAla ThrTyrProL ysIleTrpVa

CAAAGTGTCT GAAGCAGACA GCAGTAATGC AGACTGGGTC 1120
lLysValSer GluAlaAspS erSerAsnAl aAspTrpVal

ACGAAGCAGC TCAATGAAAT CAATTATGAA GACCACAAGT 1160
ThrLysGlnL euAsnGluIl eAsnTyrGlu AspHisLysL
```

TGAAGTCAGG GACTAACACC AAGAAGGCCC TCCAGGCAGT  1200
euLysSerGl yThrAsnThr LysLysAlaL euGlnAlaVa

GTACAGCATG ATGAGCTGGC CAGATGACGT CCCTCCTGAA  1240
lTyrSerMet MetSerTrpP roAspAspVa lProProGlu

GGCTGGAACC GCACCCGCCA TGTCATCATC CTCATGACTG  1280
GlyTrpAsnA rgThrArgHi sValIleIle LeuMetThrA

ATGGATTGCA CAACATGGGC GGGGACCCAA TTACTGTCAT  1320
spGlyLeuHi sAsnMetGly GlyAspProI leThrValIl

TGATGAGATC CGGGACTTGC TATACATTGG CAAGGATCGC  1360
eAspGluIle ArgAspLeuL euTyrIleGl yLysAspArg

AAAAACCCAA GGGAGGATTA TCTGGATGTC TATGTGTTTG  1400
LysAsnProA rgGluAspTy rLeuAspVal TyrValPheG

GGGTCGGGCC TTTGGTGAAC CAAGTGAACA TCAATGCTTT  1440
lyValGlyPr oLeuValAsn GlnValAsnI leAsnAlaLe
```

FIG. 2E

```
               10        20        30        40
          1234567890 1234567890 1234567890 1234567890
          ---------------------------------------------
          GGCTTCCAAG AAAGACAATG AGCAACATGT GTTCAAAGTC  1480
          uAlaSerLys LysAspAsnG luGlnHisVa lPheLysVal

AAGGATATGG AAAACCTGGA AGATGTTTTC TACCAAATGA  1520
          LysAspMetG luAsnLeuGl uAspValPhe TyrGlnMetI

TCGATGAAAG CCAGTCTCTG AGTCTCTGTG GCATGGTTTG  1560
          leAspGluSe rGlnSerLeu SerLeuCysG lyMetValTr

GGAACACAGG AAGGGTACCG ATTACCACAA GCAACCATGG  1600
          pGluHisArg LysGlyThrA spTyrHisLy sGlnProTrp

CAGGCCAAGA TCTCAGTCAT TCGCCCTTCA AAGGGACACG  1640
          GlnAlaLysI leSerValIl eArgProSer LysGlyHisG

AGAGCTGTAT GGGGGCTGTG GTGTCTGAGT ACTTTGTGCT  1680
          luSerCysMe tGlyAlaVal ValSerGluT yrPheValLe

GACAGCAGCA CATTGTTTCA CTGTGGATGA CAAGGAACAC  1720
          uThrAlaAla HisCysPheT hrValAspAs pLysGluHis
```

```
         10         20         30         40
1234567890 1234567890 1234567890 1234567890
TCAATCAAGG TCAGCGTAGG AGGGGAGAAG CGGGACCTGG   1760
SerIleLysV alSerValGl yGlyGluLys ArgAspLeuG

AGATAGAAGT AGTCCTATTT CACCCCAACT ACAACATTAA   1800
luIleGluVa lValLeuPhe HisProAsnT yrAsnIleAs

TGGGAAAAAA GAAGCAGGAA TTCCTGAATT TTATGACTAT   1840
nGlyLysLys GluAlaGlyI leProGluPh eTyrAspTyr

GACGTTGCCC TGATCAAGCT CAAGAATAAG CTGAAATATG   1880
AspValAlaL euIleLysLe uLysAsnLys LeuLysTyrG

GCCAGACTAT CAGGCCCATT TGTCTCCCCT GCACCGAGGG   1920
lyGlnThrIl eArgProIle CysLeuProC ysThrGluGl

AACAACTCGA GCTTTGAGGC TTCCTCCAAC TACCACTTGC   1960
yThrThrArg AlaLeuArgL euProProTh rThrThrCys

CAGCAACAAA AGGAAGAGCT GCTCCCTGCA CAGGATATCA   2000
GlnGlnGlnL ysGluGluLe uLeuProAla GlnAspIleL
```

```
                    10         20         30         40
           1234567890 1234567890 1234567890 1234567890
           AAGCTCTGTT TGTGTCTGAG GAGGAGAAAA AGCTGACTCG  2040
            ysAlaLeuPh eValSerGlu GluGluLysL ysLeuThrAr

GAAGGAGGTC TACATCAAGA ATGGGGATAA GAAAGGCAGC  2080
            gLysGluVal TyrIleLysA snGlyAspLy sLysGlySer

TGTGAGAGAG ATGCTCAATA TGCCCCAGGC TATGACAAAG  2120
            CysGluArgA spAlaGlnTy rAlaProGly TyrAspLysV

TCAAGGACAT CTCAGAGGTG GTCACCCCTC GGTTCCTTTG  2160
            alLysAspIl eSerGluVal ValThrProA rgPheLeuCy

TACTGGAGGA GTGAGTCCCT ATGCTGACCC CAATACTTGC  2200
            sThrGlyGly ValSerProT yrAlaAspPr oAsnThrCys

AGAGGTGATT CTGGCGGCCC CTTGATAGTT CACAAGAGAA  2240
            ArgGlyAspS erGlyGlyPr oLeuIleVal HisLysArgS
```

GTCGTTTCAT   TCAAGTTGGT   GTAATCAGCT   GGGGAGTAGT    2280
        erArgPheIl   eGlnValGly   ValIleSerT   rpGlyValVa

GGATGTCTGC   AAAAACCAGA   AGCGGCAAAA   GCAGGTACCT    2320
        lAspValCys   LysAsnGlnL   ysArgGlnLy   sGlnValPro

GCTCACGCCC   GAGACTTTCA   CATCAACCTC   TTTCAAGTGC    2360
        AlaHisAlaA   rgAspPheHi   sIleAsnLeu   PheGlnVall TGCCCTGGCT   GAAGGAGAAA   CTCCAAGATG   AGGATTTGGG    2400
        euProTrpLe   uLysGluLys   LeuGlnAspG   luAspLeuGl TTTTCTATAA   GGGGTTTCCT   GCTGGACAGG   GGCGTGGGAT    2440
        yPheLeu

TGAATTAAAA   CAGCTGCGAC   AACAAAAAAA   AAAAAAAAA     2480

AAA                                                  2483
```

```
Consensus   ..........   ......LA..   ...SC.....V.   I.GG.F.L..
Factor B    ----------   --TPWS..RP   QG..SLEG.E.K   .S.R.LO        28
C2          MGPIMVLFCI   LFLYPG..DS   AP..P-ON.N.S   .T.T.SH        39
                                          1              2

....G..L.Y   .CP.G.YP.P   ...R.C.S.G   .✩.T.....
Factor B    .E---.QA.E.   V..S.F..Y.   .VQT.T.R.T.   S.S.LKTQDQ     65
C2          GWAP.SL.T..   S..Q.L..S.   -AS..L.K.S.   Q.Q.PGATRS     78
               3            4              5   6        7

....KA.C...   .CP.P..FE    NG.Y.PR...   Y.V.....SF.
Factor B    KTVR..E.RA   IH..R.HD..   .E.W..SPY..   .N.SDEI..H    105
C2          RSLS..V.KP   VR..A.VS..   .I.T..LGS..   .P.GGNV..E    116
               8   9        10            11            12

C.DG..LRGS   ..R.C..NG.   W.G.TA.CDN   GAG.C.NPGI
Factor B    .Y..YT....   .AN.T.QV..R   .S.Q..I...   ..Y.S.....    145
C2          .E..FI....   PV.Q.RP..M   .D.E..V...   ..H.P.....    156
               13           14   15       16           17
```

FIG. 3B

```
              ..G.....G.       .....D.V.Y.  CS...L.L.GS       ..R.CQ...G.
Factor B      PI.TRKV.SQ YRLE  S.T.H  RG.T.R        QR.T  EG.S     185
C2            SL.AVRT.FR FGHG  K.R.R  SN.V.T        SE.E  GN.V     196
              18         19    20     21            22    23

WSGTEP.C.      ..YD.P..V A.A...S...      E FLS.LTE TIEGVDAEDG   225
Factor B      S.QD  SFM       T.QE.                     FLS.LTE TIEGVDAEDG
C2            I.RQ  PYS       F.ED.                   P LGT.FSH MLGATNP--T   234
              24             25

...E...RK  I.....SG..N  .YL.LD.S.S  .....F...K
Factor B      HGPG.QQK..  .VLDP.SM.    I..V..G.D.   IGASN.TGA.                265
C2            QKTK.SLG..  .QIQR..HL.   L..L..C.Q.   VSEND.LIF.                274
                          ↑                              ↗ vWF Domain
                    Proteolytic
                       Site
```

FIG. 4

Factor B vWF Substitutions

```
DPSGSMNIYL VLDGSDSIGA SNFTGAKKCL VNLIEKVASY GVKPRYGLVT   288
        26 ..L.......
        27 ...C......
        28 ......A...
        29 ..A.......
        30 ...C.Q.VSE ND
        31 ......G..IP HD

YATYPKIWVK VSEADSSNAD WVTKQLNEIN YEDHKLKSGT NTKKALQAVY   338
SMMSWPDDVP PEGWNRTRHV IILMTDGLHN MGGDPITVID EIRDLLYIGK   388
                                 34 KS. ..
                                 35 -EK F-

DRKNPREDYL DVYVFGVGPL VNQVNINALA SKKDNEQHVF RVKDMENLED   438
VFYQMID                                                  445
```

FIG. 5A

```
Factor B vWF domain  DPSGSMNIYL VLDGSDSIGA SNFTGAKKCL VNLIEKVASY    40
C2_vWF domain        QRSGHLNLYL LLDCSQSVSE NDFLIFKESA SLMVDRIFSF    40
MAC-1 vWF domain     CPQEDSDIAF LIDGSGSIIP HDFRRMKEFV STVMEQLKK-    39
CR4 vWB domain       CPRQEQDIVF LIDGSGSISS RNFATMMNFV RAVISQFQR-    39
Consensus            .P......I. L.DGS.SI.. ..F....K.. ..........    40

Factor B vWF domain  GVKPRYGLVT YATYPKIWVK VSEADSSNAD WVTKQINEIN    80
C2_vWF domain        EINVSVAIIT FASEPKVLMS VLNDNSRDMT EVISSIENAN    80
MAC-1 vWF domain     -SKTLFSLMQ YSEEFRIHFT FKEFQNNPNP ---RSLVKP-    74
CR4 vWB domain       -PSTQFSLMQ FSNKFQTHFT FEEFRRTSNP ---LSLLAS-    74
Consensus            ..........L........ ..........E......... ......SI..    80

Factor B vWF domain  YEDHKLKSGT NIKKALQAVY SMMS----WPD DVPPEGWNRT   117
C2_vWF domain        YKDHENGTGT NIYAALNSVY LMMNNQMRLL GMETMAWQEI   120
MAC-1 vWF domain     -ITQLLGR-T HIATGIRKV- -VRE----LF NITNGARKNA   106
CR4 vWB domain       --VHQLQGFT YTATAIQNV- -VHR-----LF HASYGARRDA   106
Consensus            ...H.L.... T....I..A...V. ........L. .......A..   120
```

| | | | | | |
|---|---|---|---|---|---|
| Factor B vWF domain | RHVIILMTDG | LHNMGGDPIT | VIDEIRDLLY | IGKDRKNPRE | 157 |
| C2 vWF domain | RHAIILLTDG | KSNMGGSPKT | AVDHIREILN | I--NQK--RN | 156 |
| MAC-1 vWF domain | FKILVVITDG | -EKF-GDPLG | YEDVIPEA-- | ---D----RE | 135 |
| CR4 vWB domain | TKILIVITDG | --KKEGDSLD | YKDVIPMA-- | ----D----AA | 135 |
| Consensus | ......I... | ....GDP... | ....D..I.. | ...D...R.. | 160 |

| | | | | | |
|---|---|---|---|---|---|
| Factor B vWF domain | DYLDVYVFGV | G----PLVNQV | N-INALASKK | DNEQHVFKVK | 193 |
| C2 vWF domain | DYLDIYAIGV | G----KLDVDW | REINELGSKK | DGERHAFILQ | 193 |
| MAC-1 vWF domain | GVIR-YVIGV | GDAFRSEKSR | QEINTIASKP | PRD-HVFQVN | 173 |
| CR4 vWB domain | GIIR-YAIGV | GLAFQNRNSW | KEINDIASKP | S-QEHIFKVE | 173 |
| Consensus | ....Y.IGV | G......... | .EIN..ASK. | ...H.F.V. | 200 |

| | | | |
|---|---|---|---|
| Factor B vWF domain | DMENTEDVFY | QMID | 207 |
| C2 vWF domain | DTKALHQVFE | HMLD | 207 |
| MAC-1 vWF domain | NFEALKTIQN | QLRE | 187 |
| CR4 vWB domain | DFDALKDIQN | QLKE | 187 |
| Consensus | D...AL.... | Q... | 214 |

FIG. 5B

MODIFIED COMPLEMENT PROTEASES

This application is a divisional of U.S. Ser. No. 08/177, 109, filed Jan. 3, 1994, to which priority is claimed under 35 U.S.C. § 120.

FIELD OF THE INVENTION

The invention relates to modified complement polypeptides, methods of producing such modified complement polypeptides, polynucleotides encoding modified complement polypeptides, pharmacuetical compositions comprising modified complement proteins, and methods of treating diseases related to complement activation.

BACKGROUND OF THE INVENTION

The complement system which is composed of some 20 serum proteins plays an important role in the human immune system, both in the resistance to infections and in the pathogenesis of tissue injury. Conversely, inappropriate activation of complement can result in tissue injury and disease. For example, Type II membranoproliferative glomerulonephritis is associated with activation of the alternate complement pathway, possibly by a serum factor termed "C3 nephritic factor" or "C3NeF" which acts at the same step as properdin (*Pathologic Basis of Disease,* Second Ed., 1979, Robbins SL and Cotran RS, eds., W.B. Saunders Company, Philadelphia, pp. 1142–1143). Although many of the complement proteins have been cloned and their roles in the complement system determined, no satisfactory method of controlling complement-associated disorders currently exists.

The complement system is largely regulated by the inactivation of its activated components. Activated complement components are inactivated through spontaneous decay and through their associations with specific binding proteins and/or proteases. For example, C4b-binding protein forms a complex with Factor I that proteolytically inactivates C4b, which thereby reduces C3 convertase activity and C5 convertase activity, both of which comprise C4b. Also for example, antagonist proteins may bind to complement components, such as C3b or C4b, thereby inhibiting their intermolecular association(s) with other complement components necessary to form activated complement convertase complexes.

Complement activation can account for substantial tissue damage in a wide variety of autoimmune/immune complex mediated syndromes such as systemic lupus erythematosus, rheumatoid arthritis, hemolytic anemias, myasthenia gravis and others. Inhibition of the complement system is likely to be desirable therapeutic intervention in these cases. In some instances, specific inhibition of the classical pathway alone could be preferred since long-term inhibition of the alternative pathway could lead to grave side effects.

Inhibition of complement activation could also be desirable in cases that involve tissue damage brought about by vascular injury such as myocardial infarction, cerebral vascular accidents or acute shock lung syndrome. In these cases, the complement system may contribute to the destruction of partially damaged tissue as in reperfusion injury. Highly stringent inhibition of complement for relatively brief periods might be preferred in these instances. In addition, the use of complement protease analogs with novel target specificities could reduce the activity of tissue-damaging proteins at sites of inflammation. Complement inhibition is important in the prevention of xenograft rejection. The inhibition of complement by cell-associated and soluble inhibitors is useful in protecting the transplant from damage caused by activation of endogenous complement.

Recently, a soluble form of the complement receptor CR1, a member of the regulators of complement activation protein family, has been used to inhibit various complement-mediated injuries (Weisman et al. (1990) *Science* 249: 146; Yeh et al. (1991) *J. Immunology* 146: 250; Pruitt et al. (1991) *Transplantation* 52: 868; Mulligan et al. (1992) *J. Immunology* 148: 1479). However, other regulators of complement activation already exist in soluble form and many of the complement proteins other than CR1 can be targeted to affect the regulation of the system and in different ways than producing soluble receptors.

Based on the foregoing, it is clear that a need exists for a method of preventing or controlling inappropriate complement activation that results in tissue injury and disease. This application provides the design and construction of new modified forms of complement proteases, whose administration could alter complement activation and thus have therapeutic use in humans.

SUMMARY OF THE INVENTION

The present invention provides analogs of complement proteins that are modified from the native form and have altered complement-mediated activity. Native form is defined as a naturally occurring protein sequence encoded by a mammalian, preferably human, genome. The functional modifications reside in the adjustment of the target specificity, stability, binding affinity to target, susceptibility to regulation, and/or cofactor requirements of the analog as compared to the native protein. These analogs can be used to control activation of the complement system, and thus are useful in treating a variety of pathological conditions associated with abnormal and/or excessive complement activation. For example, the complement protein analogs can be used for the treatment of autoimmune diseases, the suppression of rejection of transplants, and in the reduction in tissue damage associated with myocardial infarctions and cerebral vascular accidents, and the like.

In one aspect, the invention is directed to analogs of Factor B, C2, C1r, C1s, Factor D, and Factor I, wherein the analogs have different specificities, affinities and/or cofactor requirements as compared to the corresponding unmodified protein. In one embodiment, the invention provides complement protein analogs that exhibit a cell lysis activity that is different from the native protein. In particular, analogs of Factor B that have increased or decreased cell lysis activity, are provided. These Factor B analogs can be produced by amino acid substitutions in the SCR domain or the vWF domain with homologous regions of C2 or CR3, and other alternative modifications.

The invention provides methods of preparing the modified complement proteins or analogs. The proteins are modified by substituting one or more amino acid residues in a SCR domain or a vWF domain of the complement protein with one or more amino acid residues from a homologous region of a second protein containing at least one SCR or vWF domain. One or more SCR domains can also be replaced by the corresponding region of a second protein. The second protein can be a complement protein. Another kind of substitution involves the replacement of a protease domain in the complement protein by a protease domain from another protease which can be a member of the serine protease family.

The invention also provides modified human Factor B which exhibits increased, decreased, or undetectable complement-mediated cell lysis activity. A polynucleotide encoding a full-length human Factor B and exemplary specific sequences of the amino acid substitutions in Factor B are provided. A Factor B fragment corresponding to the Bb sequence is also provided.

In another aspect, the invention is directed to polynucleotides and host cells (or host multicellular organisms) useful in the production of these analogs. Methods of isolating and testing of the complement-mediated activity of these analogs are also provided.

In still another aspect, the invention is directed to pharmaceutical compositions wherein these analogs are active ingredients in therapeutic and prophylactic contexts.

The invention is also directed to a method of treating complement-mediated disorders using a therapeutically effective amount of a modified complement protein.

BRIEF DESCRIPTION OF THE FIGURES

FIGS. 2A through 2I shows the nucleotide and amino acid sequences of the full length human Factor B cDNA as identified by SEQ. ID NOS:1 and 2.

FIGS. 3A and 3B (SEQ ID NOS:57 and 58) compares the SCR sequences of Factor B and C2 and shows the 25 different Factor B substitutions in the SCRs (see Table 1).

FIG. 4 (SEQ ID NO:59) shows the Factor B substitutions in the vWF domain (see Table 1).

FIGS. 5A and 5B (SEQ ID NOS:60, 61, 62 and 63) shows a comparison of the vWF domain sequences of Factor B, C2, MAC-1 and CR4.

FIG. 6A shows the conserved amino acids of a typical SCR. FIG. 6B shows the organization of RCA proteins containing SCR domains.

DETAILED DESCRIPTION OF THE INVENTION

Figure 1:
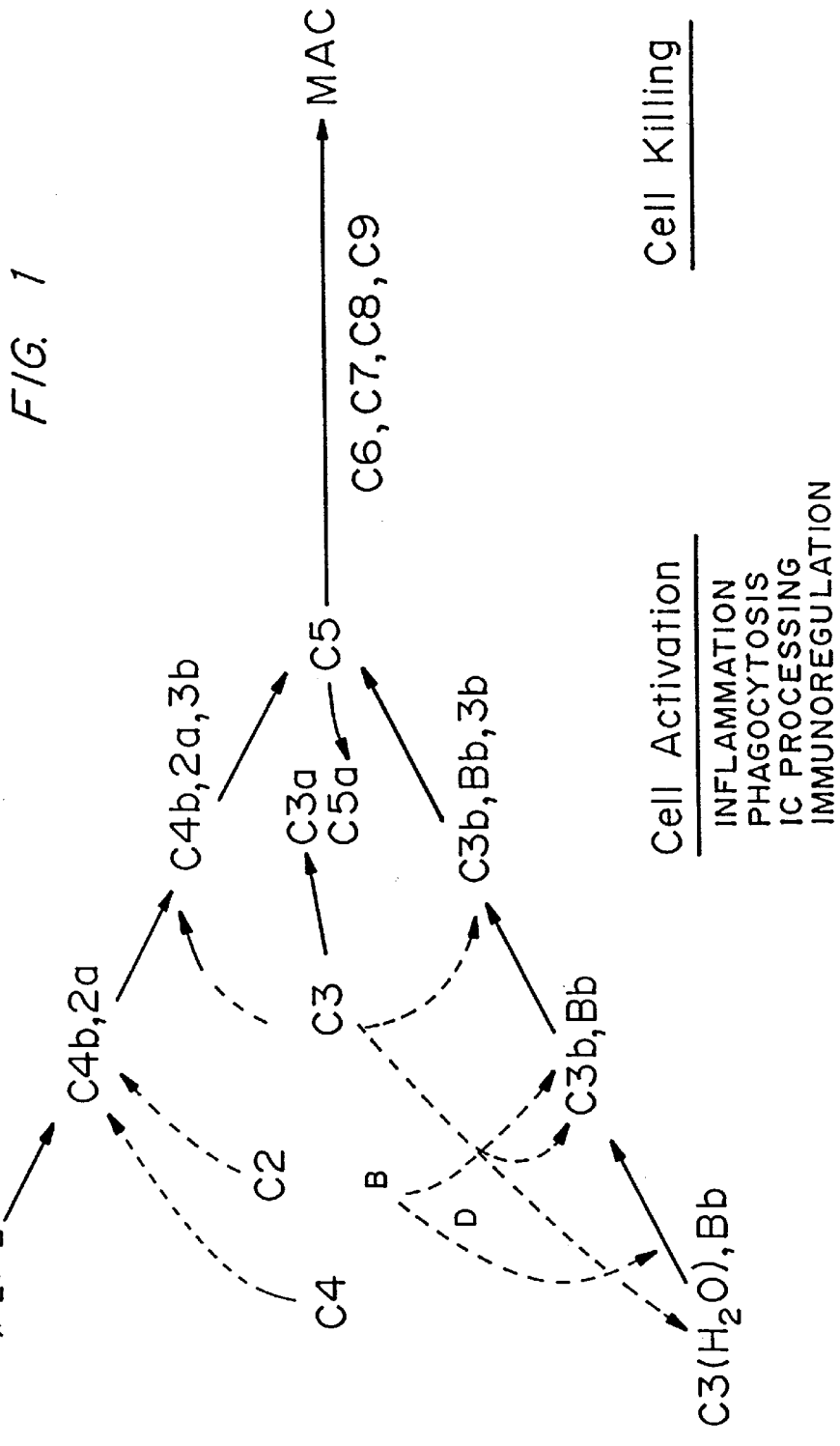
FIG. 1 is a schematic representation of the organization of the complement pathways.

The nature of the complement system is reviewed by H. J. Muller-Eberhard in: Inflammation: Basic Principles and Clinical Correlates, 2nd Ed. (Gallin, Goldstein, and Snyderman, eds.) Raven Press, Ltd., NY, 1992. For a review of the alternative pathway convertase, Factor B, Factor D, and component C2, refer to J. E. Volunakis: The Third Component of Complement Chemistry and Biology, Springer-Verlag, NY, 1990. Briefly, as set forth in these reviews and as schematically depicted in FIG. 1, there are two major pathways by which the complement system can be activated: the classical pathway or the alternative pathway. Each pathway leads to the assembly of a bimolecular protease, or C3 convertase, which cleaves a central complement component, C3, generating the fragments C3a and C3b. C3a is an anaphylatoxin with vasoactive properties, while C3b binds covalently to nearby targets to form the focus of further complement activation, potentiating inflammation and leading ultimately to immune complex clearance and/or target cell lysis.

The alternative pathway

The alternative pathway is activated by bacteria and certain cell surfaces and does not require antibody. Activation results in the direct assembly of a C3 convertase. The alternative pathway convertase is composed of C3b and a portion (Bb) of the plasma component Factor B, a 90 kDa single-chain glycoprotein zymogen. The amino acid sequence of Factor B is organized into three regions: the amino-terminal region consists of three direct short consensus repeats (SCRs, infra). Each repeat is encoded by a separate exon. The middle region is similar to the von Willebrand Factor (vWF) repeat, vWF being a glycoprotein that plays an essential role in hemostasis. This middle domain is also homologous to the middle domain of C2. The carboxy-terminal region is a serine protease domain that carries the catalytic site of the C3 convertase.

Assembly of the C3 convertase (alternative pathway convertase) begins with the association of C3b and Factor B. Factor D, a 24 kD plasma serine protease, cleaves Factor B (but only when factor B is associated with C3b) between the SCRs and the vWF domain, resulting in the dissociation of the amino-terminal region (Ba) and the formation of a proteolytically active alternative pathway C3 convertase, C3bBb.

The classical pathway

Activation of the classical pathway is initiated by the binding of C1, the first component in the complement cascade, to an antigen-antibody complex and the subsequent activation of the antibody-bound C1. C1 can also be activated by certain pathogens including HIV-1 (Ebenbichler et al. (1991) *J. Exp. Med.* 174:1417). C1 is a complex of three subcomponents—C1q, C1r and C1s, the latter two being homologous single-chain zymogens of 85 kD each. The first proteins i.e. C1r, C1s, C4, C2 and C3 in the complement cascade exist as inactive precursor molecules which when converted to active proteases by proteolytic reactions participate in cleavage of the next protein in the sequence. Thus, the activation of C1r and C1s results in a complex protease that can cleave C4 and C2. C2 has 39% sequence identity in amino acid sequence to Factor B, and is a 102 kD zymogen composed of three SCRs followed by a vWF repeat and a serine protease domain. In the $Mg^{2+}$ dependent formation of the convertase C4bC2a, a weakly-associating C4bC2 allows the cleavage of the C2 subunit by activated C1, yielding two C2 fragments. C2a and C2b. The C2b fragment, derived from the amino-terminus, dissociates while the remaining C2a fragment associates more tightly with C4b, to form the proteolytically active classical pathway C3 convertase, C4bC2a. C3 is cleaved to produce the important fragment C3b, an opsonin that binds covalently to nearby cells and macromolecules. When these reactions occur on a cell surface, they can direct the assembly of complement lytic components in the membrane. The next product of proteolysis, C5b, initiates the assembly of the membrane attack complex (MAC) by a series of protein-protein interactions that involve the components C6 to C9. Attachment of this C5b6789 complex to the membrane leads to formation of a channel that traverses the membrane permitting the flux of water and cellular contents, ultimately leading to cell lysis. C3b and C4b deposition can also result in the clearance of macromolecules: complement receptor one (CR1) on red blood cells mediates the trafficking of opsonized particles to the liver and spleen where they are destroyed by macrophages. Further effects are mediated by complement receptors CR2 and CR3, that modulate the immune response through interactions with proteolytic products of C3b.

Short consensus repeat (SCR)

Figures 6A, 6B:
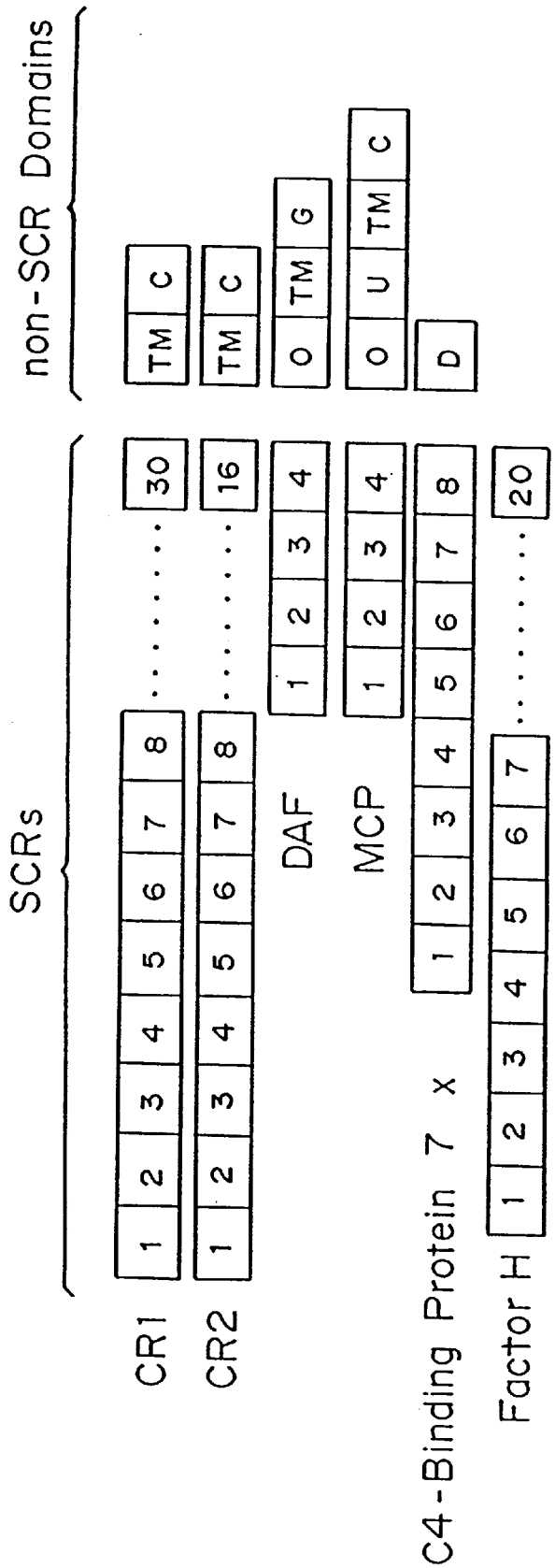
FIGS. 6A and 6B is a schematic representation of short consensus repeats (SCR).

The short consensus repeat (SCR, reviewed in Reid and Day (1989), *Immunol. Today* 10:177–180) is a motif of approximately 60 amino acids characterized by four invariant cysteines and 17 other conserved amino acids (see FIG. 6A). Two to 30 of these motifs can be found in a tandem arrays in any single complement-related protein chain (FIG. 6B). This motif is found in 12 complement-related proteins as well as many other proteins including the IL-2 receptor, Factor XIIIb of the coagulation system, lymphocyte homing receptors, and several viral proteins. These repeating units represent a major structural element in the regulators of complement activation (RCA, infra) which include two receptors, CR1 (30 repeats) and CR2 (15–16 repeats), and four inhibitors, Factor H (20 repeats), C4bp (8 repeats), membrane cofactor protein (MCP, 4 repeats), and Decay Accelerating Factor (DAF, 4 repeats). All these RCA proteins interact with activation products of C3 and/or C4. SCRs are also found at the amino terminus of the serine proteases Factor B and C2 (3 repeats), in C1r and C1s (2 repeats each), and in C6 and C7.

Regulation of the complement system

The control of the classical pathway is in part due to the strict regulation of C1 action. The proenzyme form of C1 tends to undergo autoactivation, through the proteolytic autoactivation of C1r, which then activates C1s. This spontaneous process is prevented by the association of C1r with C1-In (C1-inhibitor, a member of the serine protease inhibitor family), which is in sevenfold molar excess in the plasma. The C1r/C1-In association is disrupted when C1 is activated by interaction with immune complexes or other activators, resulting in the sequential proteolytic cleavage of C1r and C1s, yielding active C1. The active form of C1 has a half life of only 13 sec due to an irreversible covalent interaction between C1s and C1-In, inactivating the complex.

Once C3 convertases are assembled, their distribution and activity levels constitute important points for the physiological regulation of complement. High levels of the C3 convertases in the plasma can result in the turnover of all available C3 to C3b, and subsequently the loss of complement capacity. Occurrence of C3 convertases on normal cell surfaces may lead to autologous tissue damage. The most basic regulation of active C3 convertases is determined by the irreversible dissociation of C3 convertase subunits, resulting in inactivation, although C3b and C4b can be recycled. In addition, a family of complement regulators (the regulators of complement activation or RCA protein family reviewed in Hourcade et al. (1989) *Adv. Immunology* 45: 381) mediate the activity of the convertases by: 1) accelerating the dissociation of the C3 convertases, and 2) providing cofactors for the cleavage of C3b and C4b by the serine protease, Factor I. C3b or C4b cleaved by Factor I become hemolytically inactive, are no longer able to be part of active C3/C5 convertases, and become ligands for complement receptors such as CR1, CR2, CR3 and CR4. CR3, the receptor for inactive C3b or iC3b is also referred to as Mac-1 (different from MAC which is the membrane attack complex). In combination with Factor I, the RCA proteins on cell surfaces protect autologous tissues from inappropriate complement activation while soluble RCA proteins limit complement activation in the plasma. Regulation of the alternative pathway convertase, C3bBb occurs via stabilization by association with the protein properdin (C3bBbP); there is no known naturally occurring protein which stabilizes C4bC2a.

The proteolytic domains of complement work only in very restricted circumstances. C1r is autoactivated in the C1 complex only when released from C1-In. C1s works only when activated by C1r, cleaves only C4 and C2, and typically has a normal half-life of 13 seconds because of the irreversible deactivation by C1-In, a member of the plasma serine protease inhibitor family. Factor D, although active in the form found in plasma, will only cleave Factor B and only when Factor B is associated with C3b. Cleavage of C3 by the Factor B and C2 protease domains occurs only after activation and in the context of the assembled convertases; dissociated Bb and C2a subunits are alone incapable of C3 cleavage. Factor I-directed deactivation of C3b and C4b requires cofactors such as MCP, CR1, Factor H and C4b-binding protein.

Complement analogs

Complement proteases are advantageous targets for the development of therapeutic agents. Altering the vulnerability of activated C1 to C1-Inh can substantially modify the effects of the classical activation pathway, for example, by increasing the potency of the classical pathway response, or by depletion of the classical pathway components through unregulated turnover of C4 and C2. Increasing the stability of C3 convertases by altering the association between the subunits, changing susceptibility to Factor I, or altering interactions with properdin, may result in the enhanced turnover of complement components C3 and Factor B, resulting in the abrogation of both the classical and alternative complement activation pathways. Similar effects may result by abrogating the requirement of a cofactor(s) for Factor I.

Alternatively, changes in the specificity or efficiency of the protease domain of the C3 convertases or of activated C1 can dramatically alter the overall response to complement activation. For example, producing C3 convertase or activated C1 forms having protease activities with novel specificities into areas of intense complement activity can inhibit further complement activation or complement-mediated damage and/or can modulate the inflammatory response by cleaving novel target molecules. Also for example, protease analogs having decreased activities or inhibitor analogs with increased inhibition activity may be used in vivo to compete with the naturally-occurring proteins for substrates, thus dampening activation.

A further understanding of the nature and advantages of the invention will become apparent by reference to the remaining portions of the specification and figures.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of a partial-length Factor B cDNA, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I ), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein, a "complement protein" is a protein of the complement system that functions in the host defense against infections and in the inflammatory process (see Muller-Eberhard; and Volunakis, supra). Complement proteins are a group of interacting blood proteins and glycoproteins found in all vertebrates. There are at least 20 soluble plasma proteins in addition to cell surface receptors that bind complement reaction products and that occur on inflammatory cells and cells of the immune system. In addition, there are regulatory membrane proteins that protect host cells from accidental complement attack. A complement protein can be one that functions in the classical pathway, for example, C2 or one that functions in the alternative pathway, for example, Factor B. At least 6 of the proteins are proteases. For example, the proteins included in the following exemplary list are complement proteins: C1q, C1r, C1s, C2-9, Factor B, Factor D, Factor H, Factor I, CR1, CR2, CR3, CR4, properdin, C1 (Inh), C4bp, MCP, DAF, CD 59 (MIRL) and HRF. A "native" form of a complement protein is one which can be isolated from an organism such as a vertebrate and which has not been intentionally modified by man in the laboratory. A "fragment" of a complement protein is a subset of a native protein, such as a fragment that results from the proteolytic cleavage of that complement protein. For example, Factor B can be enzymatically cleaved by Factor D, resulting in two fragments: Ba which constitutes the N-terminal portion of B; and Bb which constitutes the C-terminal portion and contains the serine protease site. A complement protein "analog" as used herein refers to a structural derivative of the parent protein that does not necessarily retain all of the properties of the native (naturally-occurring) parent protein. An analog is produced by replacing or substituting amino acids of the native protein as described below. The "substitutions" or replacements typically involve naturally occurring amino acids. The substitutions can comprise one, two, or three amino acids but typically involve four to eight amino acids. Substitutions between two proteins are not restricted to identical numbers of amino acids exchanged between the two proteins. For example, Bmut 34 (see Table 1 in Examples) is a substitution of 2 amino acids in the vWF domain of Factor B with 2 amino acids in the vWF region of C2 but Bmut 35 involves a substitution of 5 amino acids of Factor B with 3 of Mac-1. If an entire domain is substituted, it typically will comprise the substitution of all of the amino acids that constitute the domain.

A polynucleotide is "operably linked" when it is placed into a functional relationship with another polynucleotide sequence. For example, a promoter is operably linked to a coding sequence if it acts in cis to modulate the transcription of the linked sequence. Generally, "operably linked" means that the DNA sequences being linked are contiguous.

A "primer" or oligonucleotide can be a single-stranded polynucleotide that may be chemically synthesized by known methods. Suitable oligonucleotides may be prepared by the phosphoramidite method described by Beaucage and Carruthers (1981) Tetr. Lett. 22: 1859, or by the triester method, according to Matteucci et al. J. Am. Chem. Soc. 103:3185 (1981), or by other methods such as by using commercial automated oligonucleotide synthesizers such as Applied Bio Systems oligonucleotide synthesizer, according to the specifications provided by the manufacturer.

The term "corresponds to" or "corresponding region" is used herein to mean that a that a polypeptide sequence is identical or substantially identical to a reference polypeptide sequence or a polynucleotide sequence is homologous (i.e. is identical, not strictly evolutionarily related) to all or a portion of a reference polynucleotide sequence. For example, a region in C2 is considered a "corresponding region" of a SCR or a vWF domain inFactor B if the polypeptide sequence in that region of C2 contains certain residues (usually invariant or occur most frequently) at defined locations, considered to be characteristic of such a domain. In this case, the characteristics of an SCR domain are as described in the above section on SCR.

"Complement-mediated activity" as used herein refers to any activity or interaction that complement proteins normally exhibit in an organism or in an in vitro assay. Complement proteins may bind antibody-antigen complexes as in the initiation of activation of the classical pathway by C1. They can associate with each other to form a bimolecular or larger complex, for example, C5b, C6, C7, C8 and C9 interact and assemble into a membrane attack complex (MAC). The association may lead to the activation of one of the components either as a result of conformational change or some other mechanism. Typically, the activation involves a first complement protein proteolytically cleaving a second protein further down the cascade, converting the second protein into an active protease. For example, the proteins C1r, C1s, C4, C2 and C3 in the complement cascade exist as inactive precursor molecules which when converted to active proteases by proteolytic reactions participate in cleavage of the next protein in the sequence.

Complement proteins or fragments of complement proteins can also be bound by soluble inhibitors or receptors on cells. For example, DAF which is directed toward C3bBb and C4b2a prevents assembly of the complexes and disassembles the formed enzymes. Other proteins such as properdin stabilizes C3bBb by associating with it.

Fragments of complement proteins ie. the proteolytic products of cleavage, for example C3a and C5a can bind to receptors on certain cells such as mast cells and basophils and induce degranulation, with release of histamine and other mediators of anaphylaxis.

Thus, "complement-mediated activity" includes in addition to cell lysis, all the functions described above such as protein-protein interactions, proteolytic activity, recognition of substrate, inhibition of assembly or inactivation of function, dissociation of complexes, anaphylatoxin activity.

The "binding affinity" of a protein refers to the tightness of the association between the protein and the component that it associates with.

The "stability" of a complement protein refers to its half-life in serum or in solution. "Isolating" a protein means identifying, separating and recovering a component of its environment. In preferred embodiments, the complement protein to be isolated will be purified from a cell culture or other synthetic environment, to greater than 95% by weight of protein, or more preferably to more than 99% by weight. Purification can be done by chromatography techniques such as affinity chromatography, gel filtration, affinity chromatography, ion exchange chromatography, HPLC, and the like. Immobilized antibodies may be used. In a preferred embodiment, the complement protein is isolated from culture supernatant by immunoprecipitation with specific antibody. For non-secreted proteins, an initial cell lysis step in appropriate detergent conditions may be employed.

A "protease domain" is that region of an enzyme that contains the active site necessary to catalyse the hydrolysis of peptide bonds in proteins, ie. split or cleave proteins.

The "serine protease family" (see Concise Encyclopedia: Biochemistry, 2nd ed. Walter de Gruyter, NY, 1988) is a group of animal and bacterial endopeptidases which have a similar mechanism of action, and a catalytically active serine residue in their active sites (eg. serine 195 in chymotrypsin). Examples of members of this family include trypsin, chymotrypsin, pancreatic elastase, thrombin, plasmin, kallikrein, as well as complement proteins such as Factor B, C1r, C1s, and C2.

A "von Willebrand Factor (vWF)" domain (also called the A-type domain) averages about 200 amino acids. It is found 3 times in vWF and once in Factor B, C2, CR3 (Mac-1), CR4 and other proteins (reviewed by Columbatti and Bonaldo (1991) *Blood* 77:2305). The overall sequence similarities among the vWF domains range from 18–64%.

Complement Protein Analogs

In accordance with the present invention, complement protein analogs are provided which are structurally modified as compared to the naturally-occurring complement proteins, and which thereby have a functional modification in one or more of the following properties: proteolytic activity; stability; binding affinity for target proteins; target specificity; susceptibility to regulatory proteins; and cofactor requirements. Modification of these properties in the complement protein analogs can directly or indirectly affect their complement-mediated cell lysis activity. These analogs can be used to modulate the complement system. The complement protein proteolytic activity, stability, binding affinity for target, susceptibility to regulatory proteins may be increased or decreased. The substrate specificity may be broadened or narrowed and the requirement for cofactor may be made more or less stringent or abolished. These modified complement proteins are produced by mutations in regions that control the above-mentioned properties.

In one aspect, the invention is directed to analogs of C1r, C1s, Factor B, Factor D, Factor I, and C2. The invention also provides methods and encoding polynucleotides for preparing these analogs, amino acid sequences encompassing the mutations, pharmaceutical compositions of these analogs as therapeutic agents in the treatment of complement related disorders, and diagnostic methods using these analogs as reagents; for example, as standards for competitive ELISA of complement proteins in serum or tissue samples and the like.

Mutations to modify the complement proteins include one or more amino acid substitutions preferably in the short consensus repeat (SCR), von Willebrand Factor (vWF) or protease domains or in any other region that binds or associates with substrates, regulatory proteins or cofactors. The amino acid substitutions comprise substituting at least one amino acid up to an entire domain or more than one domain (such as several SCRs); or a combination of the above. In additon to substitutions, additions and deletions of one or more amino acid residues or domains may be accomplished.

In one embodiment, amino acid substitutions are made in the SCR and/or in the vWF domain(s), between complement proteases and other proteins within the complement family, for example between Factor B and C2 or between Factor B and CR3. Substitutions can be performed between any two complement proteins selected from the group consisting of but not limited to the following: Factor B, Factor D, Factor I, C1r, C1s, C2, C6, C7, CR3 (Mac-1) and CR4. Examples of such substitutions are shown in Table 1 and FIGS. 2A–I, 3A–B, 4, and 5A–B. The residues in the vWF domain of human C2, numbered 13–17 in FIG. 5A, were shown by Horiuchi et al. (1991) *J. Immunol.* 142:2105) to be important for the binding of C4b by C2a. In one aspect, the focus of amino acid substitutions in C2 will be on these residues and in the homologous region of Factor B.

In another embodiment, amino acid substitutions are made between complement proteases and homologous regions of proteins outside of the complement protease family. For example, amino acids in the SCR or vWF domain of Factor B can be substituted with amino acids in homologous domains present in a non-complement protein, such as the SCR or vWF domains of the IL-2 receptor or the vWF domains of von Willibrand factor.

In another particular embodiment, the protease domain of a member of the complement protease family is substituted with the protease domain of either (a) a second member of the complement family, or (b) a member of the serine protease superfamily. An example of (a) is the substitution of the protease domain of Factor I with the protease domain of Factor B. An example of (b) is the substitution of the protease domain of chymotrypsin or elastase. Such substitutions will alter the substrate specificity of the complement protease. For example, the substrate specificity of a C3 convertase may be altered such that the C3 convertase is able to cleave a toxin instead of its normal substrate. In some variations, the analog will lack substantial protease activity but will bind to the complement component with detectable binding affinity.

Complement protein analogs may comprise glycosylation patterns which are distinct from glycosylation patterns on naturally-occurring complement components, or may lack glycosylation altogether. Glycosylation may be added to polypeptide analogs comprising glycosylation site sequences for N- and/or O-linked glycosylation in vitro, such as with a canine pancreatic microsome system (Mueckler and Lodish (1986) *Cell* 44: 629 and Walter, P. (1983) *Meth. Enzymol.* 96: 84) or the like.

In certain embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal modifications such as amidation, as well as other terminal modifications, including cyclization, may be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others.

Peptidomimetics of Complement Analogs

In addition to complement analogs consisting only of naturally-occuring amino acids, complement analog peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as a complement polypeptide, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —CH(OH)$CH_2$—, and —$CH_2SO$—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 (—$CH_2NH$—, $CH_2CH_2$—); Spatola, A. F. et al., *Life Sci* (1986) 38:1243–1249 (—$CH_2$—S); Hann, M. M., *J Chem Soc Perkin Trans I* (1982) 307–314 (—CH═CH—, cis and trans); Almquist, R. G. et al., *J Med Chem* (1980) 23:1392–1398 (—$COCH_2$—); Jennings-White, C. et al., *Tetrahedron Lett* (1982) 23:2533 (—$COCH_2$—); Szelke, M. et al., European Appln. EP 45665 (1982) CA: 97:39405 (1982) (—CH(OH)$CH_2$—); Holladay, M. W. et al., *Tetrahedron Lett* (1983) 24:4401–4404 (—C(OH)$CH_2$—); and Hruby, V. J., *Life Sci* (1982) 31:189–199 (—$CH_2$—S—); each of which is incorporated herein by reference. A particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., other complement components) to which the peptidomimetic binds to produce the therapeutic effect. Derivitization (e.g., labelling) of peptidomimetics should not substantially interfere with the desired biological or pharmacological activity of the peptidomimetic. Peptidomimetics of complement proteins may be used as competitive or noncompetitive agonists or antagonists of complement activation and function, respectively. For example, a complement protein peptidomimetic added to serum containing the naturally-occurring complement protein may compete with the naturally-occurring protein and reduce its activity (e.g., and reduce complement activation). Alternatively, a complement protein peptidomimetic may provide enhanced function or the like.

Systematic substitution of one or more amino acids of a consensus sequence with a D-amino acid of the same type (e.g., D-lysine in place of L-lysine) may be used to generate more stable peptides. In addition, constrained peptides (including cyclized peptides) comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide.

Production of Analogs

The amino acids in certain domains of the complement proteins can be "replaced" or substituted by a variety of methods including chemically synthesizing the modified polypeptides. The modified complement proteins described herein are most conveniently prepared by expression of recombinant polynucleotides, which may be readily engineered by site-directed mutagenesis, most preferably as described in Experimental Examples, infra.

For mutagenesis by recombinant nucleic acid techniques, it is desirable to obtain a polynucleotide encoding the protein to be modified such as a cDNA or genomic DNA but preferably a cDNA, or even more preferably a cDNA cloned in a vector containing a selectable marker suitable for selection in a bacterial host (for example the β-lactamase gene for selection with ampicillin). The vector can be a plasmid. Most conveniently, the vector will have the following features: a selectable marker suitable for selection in a bacterial host; a selectable marker suitable for selection in a eukaryotic host cell; an origin of replication for plasmid propagation in bacterial cells; and the cDNA operably linked to a promoter and sequences necessary for the proper transcription, translation and secretion of the protein in eukaryotic cells. If the cDNA encoding the native protein of interest is not readily available but the nucleotide sequence is available from a sequence data bank, the cDNA can be synthesized, for example, by PCR from poly-A mRNA from cells expressing the complement protein (e.g., hepatocytes), using appropriate primers based on the nucleotide sequence.

The amino acid sequences of the known complement proteins enable those of skill in the art to produce polypeptides comprising amino acid sequences corresponding to complement protein peptide sequences and sequence variants thereof. Such polypeptides may be produced in prokaryotic or eukaryotic host cells by expression of polynucleotides encoding a desired peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology. Volume 152. Guide to Molecular Cloning Techniques* (1987), Academic Press, Inc., San Diego, Calif.; Merrifield, J. (1969) *J. Am. Chem. Soc.* 91: 501; Chaiken I. M. (1981) *CRC Crit. Rev. Biochem.* 11: 255; Kaiser et al.(1989) *Science* 243: 187; Merrifield, B. (1986) *Science* 232: 342; Kent, S. B. H. (1988) *Ann. Rev. Biochem.* 57: 957; and Offord, R. E. (1980) *Semisynthetic Proteins,* Wiley Publishing, which are incorporated herein by reference).

The complement proteins, or analogs thereof, may then be purified by conventional biochemical methods known to those skilled in the art.

Assays for Determining Complement Activity

Once a complement protein analog is produced, its activity profile generally is determined. The activity profile comprises determining the biochemical properties of the analog (e.g., binding affinity to one or more complement proteins, protease activity and substrate usage, stability, oxidation resistance, and the like).

Activation of the complement cascade ultimately leads to the formation of a membrane attack complex by the terminal components, which forms a channel in the cell membrane leading to "cell lysis". Complement has been shown to be capable of mediating the lytic destruction of many kinds of cells including erythrocytes, platelets, bacteria, viruses possessing a lipoprotein envelope, and lymphocytes. As discussed earlier, either complement pathway may produce cytolytic damage. Each step of the cascade, ie. the associations, the proteolytic cleavage and activation, contributes to achieve this final outcome and complement-mediated "cell lysis activity" herein is measured by the capacity to facilitate cell lysis by the terminal complement components. For a description of complement assays, see Cooper, N. R. The complement system. In Basic and Clinical Immunology (Fudenberg, Stites, Caldwell and Wells, eds.) pp 83–95, Lange Medical Publications, Los Altos, 1980. Complement-mediated cell lysis of native complement is generally measured in vitro by assessing the ability of serum in limiting dilution to lyse sheep red blood cells sensitized with rabbit antisheep antibody (hemolysin). The red cells can be radiolabelled, for example by loading with $^{51}$Cr and lysis determined by measuring the amount of radioactivity released as detected by a gamma counter. Alternatively, the lysis of unlabelled red blood cells can be quantitated by centrifuging cell mixtures after lysis and monitoring the $OD_{414}$ of the supernatant to detect the released hemoglobin. Complement titrations of this type provide an overall measure of the integrity of the classic complement pathway and of the membrane attack mechanism. The values are expressed as 50% hemolytic complement units per ml ($CH_{50}$). One $CH_{50}$ unit is defined as the quantity or dilution of serum required to lyse 50% of the cells in the test serum.

A similar assay system is used to measure the hemolytic activity of individual complement components in isolated form or in serum. In this assay system, all the components except the one in question are supplied in excess and stringent reaction conditions are employed which are known to be optimal for each component. A example of such a cell lysis assay for Factor B is described in Experimental Examples. This use of hemolytic activity measurements for quantitation of complement components has a firm theoretical and mathematical basis, since it has been shown that the individual reaction steps of a number of the components conform to a one-hit process. Hemolytic values obtained by such titrations are typically expressed as site-forming units or effective molecules.

The pattern of depletion of complement components following treatment of serum with potential complement-activating agents may indicate the pathway of complement activation involved. Classical pathway activation depletes C1, C4, C2, C3 and C5 and, to a lesser extent, late acting components. Alternative pathway activation, leads to significant consumption of C3–C9.

Other methods of quantitating complement include single radial diffusion in agar (see Cooper above) as well as electrophoresis in SDS-PAGE and Western blotting. However, the preferable method of quantitating a complement component is a hemolytic assay to measure activity and an ELISA to measure protein concentration.

The complement-mediated cell lysis activity of a particular component can be calculated as shown in the example for Factor B and expressed as average lethal hits per cell (Z). The lysis activity of each modified component is compared to that of the native protein, derived by recombinant means, which is given a standard value of 100%. For the interpretation of the significance of the activity, see the discussion of Table 1 in Example 2. "Substantially inactive" as used herein means that cell lysis activity was undetectable within the limits of the assay system used.

The particular protein or proteins that a complement protein directly acts on or alters is referred to as a substrate of the complement protein. As discussed above, this activity is typically a proteolytic cleavage. A "target" can be a substrate or just a component that the protein recognizes and associates with. The component can be a protein, a cleavage fragment of a protein, a lipid, a cation, a sugar moiety, a membrane surface or a nucleic acid. Complement proteins display "target specificity" in that a particular complement protein can only act on a specific substrate and frequently in a specific context. For example, Factor D can only cleave Factor B and only if Factor B is associated with C3b. The target specificity of a particular complement protein can be broadened or narrowed. If cleavage of Factor B is further restricted to recognition of Factor B in association with C3b and a third component, then the target specificity of Factor D has narrowed. If Factor D is altered such that it can now bind to and cleave C2 in addition to Factor B, its target specificity has broadened. The breadth of target specificity can be determined by Western blot analysis of proteolytic products.

Therapeutic Use of Complement Protein Analogs

For therapeutic uses, pharmaceutical compositions of the complement analogs are also provided. The most potent analogs based on the in vitro assays are tested in vivo. In general, the in vitro assays are accepted as highly correlated with the corresponding in vivo activity. The "therapeutically effective amount" or appropriate dosage is determined by comparing the in vitro activity of the naturally occurring protein with that of the analog, comparing the in vitro activity of the naturally occurring protein with the in vivo activity of the naturally occurring protein, then calculating the expected in vivo activity of the analog, adjusting for any measured differences in half-life.

The analogs can be administered locally or systemically in pharmaceutically acceptable carriers such as saline, phosphate buffered saline, or a controlled release formulation. The dosage level and mode of administration of the analogs depend on the nature of the analog, the nature of the condition to be treated, and the history of the individual patient. Systemic administration is generally required, which may be by injection or by transmucosal or transdermal delivery. Administration by injection may be intravenous, intramuscular, intraperitoneal or subcutaneous. Formulations for injection are generally biocompatible solutions of the active ingredient such as Hank's solution or Ringer's solution. Formulations for transdermal or transmucosal administration generally include penetrants such as fusidic acid or bile salts in combination with detergents or surface-active agents. The formulations can then be manufactured as aerosols, suppositories, or patches. Oral administration is generally not favored for protein or peptide active ingredients; however, if suitably formulated so as to be protected from the digestive enzymes, oral administration can also be employed.

Suitable formulations for a desired mode of administration can be found in *Remington's Pharmaceutical Sciences*, latest edition, Mack Publishing Co., Easton, Pa. The dosage levels and precise formulations are obtainable by routine optimization procedures as is generally known in the art.

A composition for use in vivo generally will contain a "pharmaceutically acceptable carrier". By this is intended either solid or liquid material, which may be inorganic or organic and of synthetic or natural origin, with which the active component of the composition is mixed or formulated to facilitate administration to a subject. Any other materials customarily employed in formulating pharmaceutical are suitable. Solid carriers include natural and synthetic cloisonne silicates, for example natural silicates such as diatomaceous earths; magnesium silicates, for example talcs; magnesium aluminum silicates, for example attapulgites and vermiculites; aluminum silicates, for example kaolinites, montmorillonites, and micas; calcium carbonate; calcium sulfate; synthetic hydrated silicone oxides and synthetic calcium or aluminum silicates; elements such as carbon or sulfur; natural and synthetic resins such as polyvinyl alcohol; and waxes such as paraffin and beeswax. Examples of suitable liquid carriers include water and aqueous solutions containing oxygenated organic compounds such as ethanol. Buffers and other materials normally present in pharmaceutical preparations, such as flavoring and suspending agents, can also be present. Pharmaceutical carriers differ from typical solutions and suspensions in that they are specifically prepared for use in vivo to exclude substances that may be harmful to the host to whom the composition is administered (e.g., removal of bacterial toxins).

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Co., a standard reference text in this field.

The present invention is illustrated by the following examples. These examples are not intended to limit the scope of the claims below as many other embodiments of the invention will be apparent to those skilled in the art upon reading the description below.

EXPERIMENTAL EXAMPLES

Materials and Methods

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, injection, lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

The modified proteins described herein are most conveniently prepared using recombinant DNA techniques. Mutant complement cDNAs are constructed by site-directed mutagenesis as described below. All mutations are verified by nucleotide sequencing using the standard dideoxy chain termination method (see Maniatis et al. supra).

I. SITE-DIRECTED MUTAGENESIS

Site-directed mutagenesis is performed on cDNA inserts (i.e., human Factor B) cloned in the expression vector pSG5 using the Stratagene "doubletake double-stranded mutagenesis" kit, taking advantage of a unique XmnI restriction site in these constructs. The following protocol is taken from the manufacturer's directions:

The primers for mutagenesis are diluted in TE (to 6 pmol/$\mu$l) and stored at $-20°$ C. The mutagenesis with the Factor B clone requires 24 pmol of primer per reaction.

Target DNA is cleaved at a unique site with restriction enzyme XmnI, biotinylated with terminal transferase, and then attached to avidin-coated beads. The strands are dissociated using NaOH. Mutagenic primers and extension primers are annealed to the "captured" template strand and used to initiate the synthesis of a complementary strand. The complementary strand is dissociated from the bead and circularized using a bridging oligonucleotide, T4 DNA ligase and T7 DNA polymerase. The resulting closed circular molecules are used to transform competent bacteria. Individual isolates are obtained and checked by DNA sequencing for the desired mutation.

A. Biotinylation of Target DNA with Terminal Deoxynucleotidyl Transferase (TdT)

The desired plasmid DNA (eg. 20 $\mu$g of the Factor B/pSG5 plasmid) is linearized with XmnI and the DNA phenol-chloroform extracted, ethanol precipitated, and resuspened the final pellet to a final concentration of 1 pmole/$\mu$l in TE buffer (4 $\mu$g/ml of Factor B/pSG5 plasmids). Five pmoles of linearized DNA (4 $\mu$g control DNA; 20 $\mu$g of Factor B/pSG5 plasmid), 20 $\mu$l of 5xtailing buffer, 5 $\mu$l of biotinylated nucleotide (Bio-11-UTP), 45 Units of TdT, and water are combined to a total volume of 100 $\mu$l and spun briefly. The mixture is incubated at 37° for 30 min. The reaction is stopped with 2 $\mu$l of 0.5 M EDTA, pH 8.0. The DNA is precipitated and washed with 70% ethanol, then pelleted and lyophilized. The pellet is resuspended in wash buffer to 1 pmole/50 $\mu$l. (Add 250 $\mu$l to control and to Factor B/pSG5 plasmids.) This material may be stored at $-20°$ or used immediately.

B. Coupling of Biotinylated DNA to Avidin-Coated Beads 1 pmole of biotinylated ends/50 $\mu$l of beads is used. 50 $\mu$l of avidin-coated beads are pelleted by spinning for 30 sec in a microfuge and the supernatant discarded. The pellet is resuspended in 100 $\mu$l of 1 M NaCl and the beads pelleted as before. The beads are washed twice in 100 $\mu$l of wash buffer each time and pelleted. The bead pellet is resuspended in 50 $\mu$l of biotinylated DNA solution (1 pmole of biotinylated DNA in wash buffer) and incubated at 37° for 1 hr. with periodic resuspension of the beads during the incubation. The beads are pelleted and washed in 100 $\mu$l wash buffer.

C. Mutagenic Strand Extension

The DNA is denatured by resuspending the coupled beads in 50 $\mu$l of denaturing solution (0.2M NaOH and 0.2 mM EDTA) and incubating at RT for 15 min. During the incubation periodically resuspend the beads. A series of 10 1.5 ml tubes with 50 μl of denaturing solution and 10 μl of Tris, pH 7.5 in each tube is set up and 5–14 μl of 1 M HCl is added to determine the exact amount needed to neutralize the reaction. The final pH must be between 7 and 8. The solution is neutralized by adding 10 μl M Tris (pH 7.5) followed by the amount of 1M HCl determined above and the beads pelleted. The beads are washed by adding 100 μl of wash buffer and gently mixing and collected by spinning for 30 sec and discarding the supernatant. The beads are resuspended in 50 μl of 2× extension buffer. Both the extension and mutagenic oligonucleotides (8.4 pmole, 50 ng, 0.5 μl XmnI extension primer for Factor B/pSG5 plasmids; 24 pmoles, 4 μl, of 33 base mutagenic primers) are added to the test reaction(s). To the control reaction, add 100 ng (1 μl) of XmnI extension primer and 400 ng (4 μl) of Blue mutagenic primer and mix. Annealing is done in a 65° C. water bath. 43.5 μl of water is added to the test reactions to a final volume of 98 μl and 43 μl water added to the control reaction. T4 DNA ligase (1 μl,4 U) and 0.5 μl of T7 DNA polymerase (1.5 U) are added to each reaction and mixed. The reaction is incubated at 37° for 30–60 min., periodically resuspending the beads. The beads are pelleted.

D. Recircularization

The DNA is denatured by resuspending the beads in 50 μl denaturing solution (0.2 M NaOH, 0.2 mM EDTA) and incubating at RT for 15 min. Neutralization is done by adding 10 μl of 1 M Tris (pH 7.5) and the amount of 1M HCl determined previously. The beads are spun for 1 min, and the supernatant which contains the ss DNA is saved while the beads are discarded. If the pH is greater than 8, adjust by adding 1 μl of 1 M HCl. This DNA solution may be used immediately or stored at −20°. In a microfuge tube, 15 μl of 2× extension buffer and 5 μl of mutant ssDNA are combined. 100 ng Xmn I bridging primer is added to control (1 μl) and 48 ng (0.5 μl) to the experimental Factor B/pSG5 reactions. The sample is transferred to a 65° C. bath, then allowed to cool slowly to 35° over 20–30 min. Water is added to a final volume of 28 μl (7 μl to the control reaction and 7.5 μl to the Factor B/pSG5 reactions. 1 μl of T4 DNA ligase (4U) and 0.5 μl of T7 DNA polymerase (1.5 U) are added and mixed and the reaction incubated at 37° for 30 min–1 hr.

E. Transformation

XL1-Blue cells are used for transformation following the manufacturer's directions. The control requires a cell line with an efficiency of $10^9$ transformants/μg DNA that in addition exhibits α-complementation. The XL1-Blue cell line is propagated on LB agar plates with 50 μg/ml ampicillin, and treated with 40 μl of 100 mM IPTG and 100 μl of 2% X-gsl.

II. EXPRESSION OF RECOMBINANT PROTEINS

Cos-7 cells were used to express the mutant proteins but other suitable host cells known to those skilled in the art can be used. The DNA can be introduced into host cells by standard techniques for transfecting eukaryotic: cells such as lipofection, electroporation, calcium phosphate precipitation, DEAE dextran or protoplast fusion.

The proteins synthesized by the transfected cells can be labelled 48 hours after transfection by biosynthetic labelling with $^{35}$S-cysteine for 4 hr to overnight (see Johnstone and Thorpe, Immunochemistry in Practice, Blackwell Scientific Publications, Boston, 1982). The proteins can be recovered from the supernatant for PAGE analysis by immunoprecipitation with the appropriate antibody bound to Staph A agarose beads. PMSF and EDTA made in 0.5% NP-40 are used as protease inhibitors. Superwash for washing the immunoprecipitate pellets is prepared as follows: per 500 ml, need 465 ml PBS, 5 ml NP-40 (to 1%), 0.5 gm Na deoxycholate (to 0.1% w/v), 5.0 ml 10% SDS (to 0.25% w/v) 10.52 gm NaCl, 25 ml 100 mM EDTA buffer.

III. QUANTITATION OF Factor B BY ELISA

In this section, an ELISA assay is described to quantitate human complement Factor B utilizing a Factor B monoclonal antibody anti-Ba or Bb), a goat anti-factor B polyclonal antibody (IgG), and peroxidase-conjugated rabbit anti-goat IgG polyclonal antibody.

Preparing Plates:

Purified anti-Bb or anti-Ba monoclonal antibody [Quidel] is diluted to 2 μg/ml (2μl/ml) in PBS. Within 5 min add 100 μl of the diluted antibody to each well, seal the plates and incubate O/N at 4° C. The antibody solution is removed by aspiration and 300 μl of blocking buffer added to each well. Plates are resealed and incubated for at least 1 hr at 37° C.

Sample Preparation and Incubation:

A standard curve can be constructed from serial dilutions of commercially obtained Factor B [Quidel, 1.1 mg/ml, 2× dilution series-each consisting of 1 μl to 1.1 ml in sample/diluent buffer, and successive dilutions of 25 μl to 475 μl to yield 50 ng/ml. Serial dilutions to 25 ng/ml, 12.56 ng/ml, 6.25 ng/ml, 3.12 ng/ml, and 1.56 ng/ml are done. Two controls with only buffer accompany each series of six Factor B standard dilutions. Normal human serum is diluted 1/8000 (1 μl sample plus 8 ml Sample/Conjugate Diluent) and serially diluted to 1/16 K, 1/32 K and 1/64 K. Cos supernatants can be diluted 1/16 (25 μl to 375 μl) followed by three serial dilutions (1/32, 1/64, and 1/128). The A14E control supernatant is diluted to ½ (400 μl to 400 μl) with serial dilutions to ¼, ⅛ and 1/16. If needed, heat-deactivated fetal calf serum may be diluted to 4% in PBS. All samples, standards and controls are run in duplicate. Remove blocking buffer from plate by aspiration and wash 3×250 μl with washing buffer. Pipette 100 μl of standards, samples and controls into wells in duplicate. Seal plates and incubate at 37° C. for 2 hr. Dilute absorbed goat anti-factor B polyclonal antibody [Incstar, IgG fraction, 12.9 mg/ml] to 1/10 K (1 μl in 10 ml) in Sample/Conjugant Diluent. Goat anti-factor B (100 υ) is added to each well and incubation carried out for 1 hr at 37° C. Peroxidase-conjugated rabbit anti-goat IgG [Jackson Immunoresearch Laboratories] is diluted 1/15 K (1 μl in 15 ml of Sample/Conjugant Diluent) and stored, in the dark, for no more than 6 hr prior to use. To each well, 100 μl conjugate are added and the reaction incubated for 1 hr at 37° C.

Preparation and Use of Chromogen

For each plate, 11.4 ml substrate buffer stock and 0.6 ml Chromagen stock are mixed. Wash wells 5×. Add 100 μl chromagen solution to each well and incubate for 10 min at RT. Plates are read immediately.

Reading Plates

The plate may be read with a Dynatech MR700 Reader with these settings:

OPTION 1.2
MODE dual
REFERENCE WAVELENGTH 5 (630 nm)
TEST WAVELENGTH 2 (450 nm)
THRESHOLD 1.99
CALIBRATION 1.00

Solutions and Reagents

All solutions here are stored at 4° C. unless indicated otherwise. The content of the following reagents are as follows:

(a) Blocking Buffer (1% BSA and 0.1% tween 20 in PBS)
(b) Sample/conjugate diluent (4% BSA and 0.25% NP40 in PBS)

(c) Wash Buffer (PBS with 0.05% Tween 20)
(d) Chromagen Stock (4% ortho-phenylenediamine dihydrochloride (OPD) in MilliQ $H_2O$.
(e) Substrate buffer stock (0.00225% $H_2O_2$ in Citrate Phosphate)
per 250 ml (20 plates), mix
1.28 g $Na_3C_6H_8O_7.2H_2O$ (Citric Acid Trisodium dihydrate)
2.3 g $Na_2HPO_4$ (Dibasic Sodium Phosphate Anhydrous)
0.188 ml 30% $H_2O_2$
To pH 6.5 with about 22 drops of 85% phosphoric acid ($H_3PO_4$)
(f) Chromagen working solution (use within 15 min)
per plate
11.4 ml Substrate buffer stock
0.6 ml Chromagen stock.

IV. ASSAY OF HUMAN Factor B BY CELL LYSIS

In this procedure, sheep erythrocytes are obtained already coated with antibody and complement components C1 and C4 (EA14) and then coated with C3b using the classical pathway (EAC1423). Addition of EGTA inhibits further activity of C1 and C2, the complexes are allowed to dissociate (EAC43b), and Factor B activity is measured by the capacity to facilitate cell lysis by the terminal complement components.

Preparation of Sheep EAC1423 Cells

Sheep EAC14 (Diamedix Corp., Miami, Fla., Cat # 789-053, $10^9$/ml, 2 ml/vial) are resuspended by gentle shaking. 0.5 ml are removed with a 3 ml syringe and 21 gauge needle and transferred into a 12 ml corex testtube. The sample is centrifuged (2,000 rpm for 10 min at 4° C., Beckman J-6 centrifuge, 824 g), and the supernatant is removed by vacuum aspiration. The pellet is gently resuspended with a pipetter into about 0.5 ml of DGVB++, brought up to 5 ml of DGVB++, and centrifuged as above. The pellet is resuspended in 5 ml of DGVB++, spun, (The cells are washed one more time if the supernatant is not clear) and resuspended in 0.47 ml DGVB++(to 0.5 ml total volume) and kept at 4° C.

A C2+C3 mixture is prepared by adding 50 $\mu$l of purified C3 (1 mg/ml, Quidel) and 100 $\mu$l C2 (suspended in distilled water to 2,000 units/ml, Diamedix) to 350 $\mu$l of DGVB++ and storing at 4° C.

In separate tubes, the cells and C2+C3 mixture are incubated at 30° C. for 5 min. The cells are swirled at 30° C. while the C3+C3 mixture is added dropwise. The mix is incubated at 30° C. for 30 min, with gentle mixing every 5 min.

The mixture is centrifuged as above and the pellet is resuspended in 5 ml 10 mM EDTA buffer. The cells are centrifuged and resuspended in 0.5 ml of 10 mM EDTA buffer and incubated at 37° C. for 2 hr. This allows decay of the classical pathway C3 convertase and leaves EAC43b.

The cells are washed twice in 10 mM EDTA buffer and twice in Mg++EGTA buffer. Before the last centrifugation the $OD_{414}$ of a 1/30 dilution of cells is measured (30 $\mu$l into 870 $\mu$l distilled water) and the cells are resuspended to a calculated final concentration of $10^8$/ml ($OD_{414}$ of 1/30 dilution=0.29. Cells are stored at 4° C. and must be used within 2–3 days).

Reagents, Standards and Samples

Purified Factor B (Quidel) may be used diluted to 5, 10, 20 and 30 ng/ml in Mg++EGTA (1 $\mu$l to 1.1 ml; 30 $\mu$l, 20 ml, 10 $\mu$l, and 5 $\mu$l to 1 ml). Normal human serum can be diluted to 1/2500, 1/5,000, 1/10,000 and 1/20,000 in Mg++EGTA buffer (2 $\mu$l to 5 $\mu$l followed by serial 500 $\mu$l to 500 $\mu$l dilutions). Transfected Cos supernatants derived from cells secreting Factor B or modified forms of Factor B may be diluted to 5 and 10 ng/ml.

Assay of Factor B Activity For each determination, 100 $\mu$l of EA3,4 cell mixture ($10^7$ cells), 50 $\mu$l purified Factor D (Quidel, 5 ng/50 $\mu$l, a 1 $\mu$l to 1 ml dilution of 0.1 mg/ml in Mg++EGTA buffer), 50 $\mu$l P (Quidel, 45 ng/50 $\mu$l, a 1 $\mu$l to 1.111 ml dilution of 1.0 mg/ml in Mg++EGTA buffer) and 50 $\mu$l Factor B source or standard are added to a 16 by 100 mm glass testtube and incubated at 30° for 30 min. A negative control sample is employed which substitutes 50 $\mu$l DGVB++ buffer in place of a Factor B source, and also an appropriately diluted supernatant derived from Cos cells transfected with some other construct (for example, Factor B cloned in the nonsense direction in the same vector). Additional controls consist of cells with 450 Ml of distilled water, and cells with 450 $\mu$l of DGVB++ buffer.

Samples are chilled in an ice bath, treated with 300 ml of 1/40 CEDTA (except for the 450 $\mu$l distilled water and the 450 $\mu$l DGVB++ buffer controls), and incubated at 37° with gentle shaking for 1 hr. Samples are centrifuged at 2,000 rpm for 5 min, 400 $\mu$l supernatant is removed, mixed with 400 $\mu$l distilled water, and the $OD_{414}$ is determined.

Calculation of Factor B Activity

OD'=OD (Sample)−OD (cells+D,P,CEDTA,Mg++EGTA)

Y=% lysis=OD'/OD (distilled water)

Z=average lethal hits per cell =calculated from the Poisson distribution or the table that follows using 1−Y as the parameter.

Z should be linear in the range of measurement.

Solutions (a) 10 mM MG++EGTA Buffer

Prepare 100 ml DGV w/out metals:
Dissolve 2.5 gm dextrose (d-glucose) into about 50 ml MilliQ water. Boil 0.1 gm gelatin in about 15 ml MilliQ water until dissolved and add to dextrose solution. Add 10 ml of 5× Veronal solution and bring to 100 ml.
Mix 83 ml of DGV w/out metals with
10 ml 100 mM EGTA stock
0.350 ml 2 M $MgCl_2$ stock
6.65 ml MilliQ water
Add NaOH to pH 7.3–7.6 (about a drop of 10 N).

(d) DGVB++ Buffer

To prepare, boil 0.5 gm gelatin in about 15 ml MilliQ water until dissolved. Add 50 ml 5× Veronal, 12.5 gm dextrose, 0.25 ml 2M $MgCl_2$ stock, and 0.25 ml 0.3 M $CaCl_2$ stock.
Bring to 500 ml with MilliQ water.

V. FACTOR B C3b-SEPHAROSE BINDING ASSAY

Preparation of C3b-Sepharose Beads

To prepare, add 3.0 ml 1 mM HCl to 1 gm CNBr-activated Sepharose beads (Pharmacia Sepharose 4B) and incubate at RT for 20 min. The beads are washed 3×40ml 1 mM HCl (centrifuge at 1,000 rpm for 5 min at 4° C.) and resuspended in 10 ml BBS, then washed 2× with BBS. The volume of the beads is adjusted to 3 ml with BBS. Three ml of 1 mg/ml C3b (or BSA) are prepared in BBS and the OD at 280 nm measured. The protein solution is mixed with the beads and incubated O/N at 4° C. on a rotator. The beads are centrifuged and the supernatant saved (Determine % bound as explained below). The beads are washed with cold BBS until the OD of a 1:4 dilution of the supernatant is less than 0.02. The beads are incubated in fresh 1 M ethanolamine, pH 8.0 for 2 hr at RT with rotation, then washed 2× with cold BBS and store at 4° C. in BBS with 0.1% $NaN_3$.

Quantitation of Ligand Bound to Beads

To quantitate, measure the OD at 280 nm for the following dilutions of the supernatants from step 5 of "preparation of C3b-Sepharose Beads":

| | |
|---|---|
| Incubation Medium | 1/8 |
| 1st Wash | 1/8 |
| 2nd Wash | 1/4 |
| 3rd Wash | 1/4 |
| 4th Wash | 1/4 |

Washes can be discontinued once the OD of 1/4 dilution is less than 0.02.
The % of the protein incubated bound to the beads is calculated. Protein quantition is given by the following equation:

mg protein=(diln Factor)(OD280)(volume)/protein specific constant

| | | |
|---|---|---|
| Protein constants: | C3 | 0.970 |
| | BSA | 0.667 |
| | IgG | 1.400 |

Protein bound=mg protein recovered in step 5 supernatant/mg protein incubated with beads (from step 3).
Solutions
  (a) Borate Buffer Saline (BBS)—100 mM boric acid/25 mM borax/75 mM NaCl.
  (b) 1 mM ethanolamine, pH 8.0.
Sample Preparation
  Cos supernatants are diluted to 10 ng/ml Factor B (this would have been determined previously by ELISA) to 75 mM salt (cell culture media=150 mM NaCl): Dilute 50 μl of supernatant with 50 μl distilled water. Subsequent dilutions are carried out with either 1/2 PBS or with DGVB++, leading to a final dilution volume of at least 1 ml each.
Measurement of C3b-Sepharose Binding
  One ml of previously prepared beads (at 150 mM salt) are washed 2–3 times in a corex tube (10 ml 1/2 PBS or DGVB++; 1000 rpm, 2 min, 4° C.) and resuspended into 1 ml of buffer. 200 μl of suspended beads are measured into microfuge tubes, spun for 5", and the supernatants are discarded. 250 μl of sample is added to each tube and mixed. The tubes are mixed at RT for an hour with a circular rotator, spun down, and the supernatants are stored at 4° C. An ELISA is employed to determine the fraction of Factor B bound to the beads, making use of the supernatants prior to bead binding as positive controls and buffer as a negative control.
Rejuvenation of Beads
  Beads are washed in 1/2 PBS+450 nM NaCl with rotation (1 hr, RT), centrifuged and resuspended 1–2 times in 10 ml PBS, resuspended in original volume of PBS, and stored at 4° C. in PBS supplemented with 0.02% NaN$_3$.

Example 1
Biosynthesis of cDNA-encoded human Factor B

Although the amino acid sequence of the human Factor B protein has been established, only a partial cDNA sequence, lacking the region encoding the amino-terminal residues, has been reported. Thus, a full length human Factor B cDNA was isolated from a size-selected, oligo dT-primed, Lambda ZAP II human acute phase liver cDNA library using a partial human Factor B cDNA clone (pBfA28, Mole et al. (1984) *J. Biol. Chem.* 259: 3407) as a probe. About 1 of every 1000 plaques hybridized to the partial Factor B probe. Several of these isolates were selected, based on additional hybridization at low stringency to oligonucleotide probes corresponding to the 5'-most region of the published Factor B sequence, and were subjected to Southern blot analysis with the pBfA28 probe. Several of these isolates, exhibiting predicted EcoR1 fragments of 1900 and 600 bp homologous to Factor B, were chosen for the in vivo excision procedure which is a feature of Lambda ZAP II clones. The insert of one of the resulting plasmids, A14, was sequenced completely in both directions.
Subcloning Factor B cDNA into an expression vector
  The complete A14 Factor B cDNA insert was excised from its plasmid by partial digestion with EcoR1 and inserted into the EcoR1 site of expression vector pSG5 (Stratagene, La Jolla, Calif.) and used to transform *E. coli* strain DH5α (BRL, Bethesda, Md.). Clones were isolated that carried the Factor B cDNA in the sense (clone A14D) and the nonsense (clone A14E) directions.
  The A14 Factor B cDNA insert was excised from its plasmid with restriction enzyme EcoR1 and inserted into the EcoR1 site of expression vector pSG5 (Green et al., *Nucl. Acids Res.* 16:369, (1988). Clones were isolated that carried the Factor B cDNA in the sense (clone A14D) and the nonsense (clone A14E) directions. Cos cell cultures were transfected with either A14D or A14E DNA and cell supernatants were assayed by ELISA (see Methods below) for the presence of human Factor B protein. By this criteria, the A14D-transfected cells produced up to 400 ng/ml Factor B in 48 hr while the A14E negative control produced less than 5 ng/ml. There was no detectable Factor B in the untransfected culture media.
  Further analysis was performed with transfected cells labelled with $^{35}$S-methionine. Supernatants from A14D-transfected cells underwent immunoprecipitation with goat anti-human Factor B. PAGE analysis followed by autoradiography revealed a predominant band of 90 kDa in apparent molecular weight, the appropriate position for mature human Factor B.
  Supernatants of the transfected Cos cells were assayed for biochemical activities associated with Factor B (see Method above). One method determines the capacity for cell supernatants to induce alternative pathway-dependent cell lysis in a Factor B-deficient in vitro system. A second method measures the binding of Factor B synthesized by transfected cells to C3b bound to Sepharose beads.
Expression and biosynthetic labelling of recombinant Factor B
  Plasmid DNA was isolated using the Wizard Mini-Prep DNA isolation kit (Promega, Madison, Wis.). SV40-transformed green monkey kidney cells (COS-7) were maintained as described (Krych et al., 1991). Transfections were performed with Lipofection Reagent (BRL, Bethesda, Md.; Felgner et al., 1987).
  Biosynthetic labeling was begun 48 hrs after transfection (Krych et al., 1991) with $^{35}$S-cysteine (Dupont, 1075 Ci/mmole, 10 mCi/ml) and allowed to continue for 4–16 hrs. For immunoprecipitation, samples were first precleared with protein A-agarose (Boehringer Mannheim Biochemicals, Indianapolis, Ind.) and then incubated with goat anti-factor B polyclonal antibody [Incstar, IgG fraction, 12.9 mg/ml] or normal goat serum (Sigma Chemical, St. Louis, Mo.). Immune complexes adsorbed to protein A-agarose were washed twice with PBS containing 360 mM NaCl, 5 mM Na$_2$EDTA, 1% NP-40, 0.1% Na deoxycholate, 0.25% SDS, and twice with PBS containing 1% NP-40. Samples were eluted in 40 μl 3× dissociation buffer and analyzed by SDS-PAGE (10%; Laemmli, 1970) with molecular weight standards (Bio-Rad; Richmond, Calif.), utilizing Amplify (Amersham) followed by autoradiography.

ELISA Determinations

Nunc MaxiSorp microtiter plates (VWR; Chicago, Ill.) were coated with murine anti-human Factor Bb monoclonal antibody (Quidel catalog #A227; San Diego, Calif.); 2 µg/ml, 100 µl/well in PBS, O/N at 4° C.), blocked with 1% BSA, 0.1% Tween 20 in PBS (1 hr, 37° C.), and washed with PBS, 0.05% Tween 20. Factor B standards were dilutions of commercially purified Factor B protein (Quidel, San Diego, Calif.). Dilutions were performed with 4% BSA and 0.25% NP40 in PBS. Standards, controls and samples were incubated in wells for 2 hrs at 37° C. After washing, wells were treated with 100 µl of a 1/10,000 dilution of goat anti-human Factor B polyclonal antibody (see above) and incubated for 1 hr at 37° C. Wells were washed, treated with 100 µl of a 1/15,000 dilution of peroxidase-conjugated rabbit anti-goat IgG (Jackson Immunoresearch Laboratories, West Grove, Pa.), and incubated for 1 hr at 37° C. Color was developed using 100 µl of freshly made 0.2% ortho-phenylenediamine and 0.0214% $H_2O_2$ in 16.5 mM sodium citrate/61.5 sodium phosphate, pH 6.5. Absorbance was read in a microplate reader (Dynatech, Chantilly, Va.). Standards, samples and controls were assayed in duplicate. By this method Factor B levels could be measured as low as 3 ng/ml.

Factor B-dependent cell lysis assay Sheep erythrocytes were obtained pre-coated with antibody, guinea pig C1 and human C4b (Diamedix Corp., Miami, Fla.; $10^9$/ml; catalog #789-053). 0.5 ml cells were washed twice (5 ml DGVB++ [2.5% Dextrose, 0.1% gelatin, 1.0 mM $MgCl_2$, 0.15 mM $CaCl_2$, 71 mM NaCl, 0.051% Na-5'-5"-diethyl barbiturate, pH 7.35], 4° C.), resuspended to 0.5 ml, incubated at 30° C. for 5 min and treated with C2 and C3 [50 µl of purified human C3 (1 mg/ml, Quidel, San Diego, Calif.), 100 µl purified human C2 (2000 units/ml, Diamedix, Miami, Fla.), 350 µl DGVB++, preincubated for 5 min at 30° C.]. The mixture is incubated at 30° C. for 30 min, with gentle mixing every 5 min to allow the assembly of active convertases (C2aC4b) and the coating of the cells with C3b; the mixture is centrifuged, the pellet resuspended in 0.5 ml of 10 mM EDTA buffer and incubated at 37° C. for 2 hr to allow dissociation of the active convertases and inhibit the production of new convertases. The cells were washed twice in 10 mM EDTA buffer [10 mM $Na_2EDTA$, 0.1% gelatin, 128 mM NaCl, 0.092%, Na-5'-5"-diethyl barbiturate, pH 7.35], twice in 10 mM Mg++ EGTA [10 mM $Na_2EGTA$, 10 mM $MgCl_2$, 2.075% Dextrose, 0.083% gelatin, 59 mM NaCl, 0.042% Na-5'-5"-diethyl barbiturate, pH 7.3–7.6] buffer and resuspended to a calculated final concentration of $10^8$/ml ($OD_{414}$=8.7). They were stored at 4° C. and used within 2 days.

Purified Factor B (Quidel) was used as a standard. COS supernatants were diluted in Mg++EGTA buffer to Factor B levels of 10 and 20 ng/ml as determined by ELISA. For each determination, 100 µl of prepared (C3b-coated) sheep erythrocytes, 50 µl Factor D (5 ng in 50 µl Mg++EGTA buffer; Quidel), 50 µl Factor P (45 ng in Mg++EGTA buffer; Quidel) and 50 µl Factor B source or standard were mixed together and incubated at 30° C. for 30 min. A negative control was employed which substituted 50 µl DGVB++ buffer in place of the Factor B source. Additional controls consisted of cells mixed with 450 µl of distilled water (complete cell lysis), and cells mixed with 450 µl of DGVB++ buffer (no cell lysis).

Samples were chilled in an ice bath, treated with 300 µl of a 1/40 dilution of guinea pig serum (Colorado Serum Co., Denver, Colo.) in 40 mM EDTA buffer [40 mM $Na_2EDTA$, 0.1% gelatin, 85 mM NaCl, 0.061%, Na-5'-5"-diethyl barbiturate, pH 7.35], (except for the 450 µl distilled water and the 450 µl DGVB++ buffer controls), and incubated at 37° C. with gentle shaking for 1 hr. Samples were centrifuged at 2,000 rpm for 5 min (J-6 centrifuge, Beckman), diluted 2× with distilled water, and $OD_{414}$ determined.

To calculate the Z value for each sample (average number of productive lytic sites per cell), OD' was calculated by subtracting the OD of the 50 µl negative control from the sample OD. Percent lysis (Y) was determined by dividing the OD' of the sample by the OD' of the distilled water control. Z was calculated from the Poisson distribution using 1−Y as the independent variable.

C3b-Sepharose Binding Assay

C3b or BSA (Biocell Laboratories, Carson, Calif.) was coupled to cyanogen bromide-activated Sepharose (Sepharose 4B, Pharmacia, Piscataway, N.J.) at a ligand concentration of 1 mg/ml (Dykman et al., 1983a; Dykman et al., 1983b). Affinity chromatography was performed essentially as described (Dykman et al., 1983a; Cole et al., 1985) using 0.10 ml of packed beads per 0.25 ml sample and DVGB++ buffer. COS supernatants were diluted 1:1 in distilled water (to 75 mM NaCl) before dilution in buffer. Eluates were analyzed by ELISA for unbound Factor B and compared to the diluted samples.

Example 2

Construction and Assay of Factor B Analogs

Various mutated forms of human Factor B were constructed as described below and tested for cell lysis activity as described in Example 1. Table 1 shows the analogs constructed and the effects on cell lysis obtained. In Table 1, the modifications are shown by the number of the amino acid and the conversion effected. They are also shown in FIGS. 3A–B and 4.

Site-directed mutagenesis

Two oligonucleotide-directed methods were employed to mutagenize Factor B/pSG5 constructs directly. The manufacturers' protocols were closely followed in both cases and mutations were confirmed by sequencing.

In the first method (doubletake double-stranded mutagenesis, Stratagene, La Jolla, Calif.), a unique vector Xmn I restriction site was utilized to cut parental plasmids. The resulting 3' ends were biotinylated and bound to avidin-coated beads. Mutant strands were synthesized by T7 polymerase and T4 ligase utilizing mutagenic primers (Table 1), extension primers and bead-bound parental template. DNA was dissociated and the mutagenic strands purified from the parental strands by centrifugation. Mutant plasmids were completed by T7 polymerase and T4 ligase utilizing a bridging primer. DNA was used to transform competent *E. coli* strain DH5α (BRL, Bethesda, Md.) and transformants were grown on LB plates supplemented with ampicillin.

In the second method (transformer site-directed mutagenesis, Clontech, Palo Alto, Calif.), simultaneous mutagenesis of a Factor B site with a mutagenic primer and a unique Xba I vector site with a selection primer (5'-Phosphate-GGAAGCGGAAGAGTCGCGAGTCGACCAGACATG-3') (SEQ ID NO:3) formed the basis of efficient selection of mutant plasmids: Parental plasmids (grown in *E. coil* strain BMH 71-18 mutS) were denatured by alkaline treatment, neutralized, and mutant strands were synthesized by T4 polymerase and T4 ligase utilizing mutagenic primers (Table I) and the selection primer. DNA was digested with Xba I and used to transform competent BMH 71-18 mutS. A mixed population of DNA was isolated from the transformant pool and cut with Xba I. DNA was used to transform competent *E. coli* strain DH5α (BRL, Bethesda, Md.) and transformants were grown on LB plates supplemented with ampicillin.

In general, mutations utilized were substitutions of amino acids from homologous regions of other proteins. In principle, the substitution of amino acid residues important for activity of one protein into the homologous region of a second, structurally and functionally related protein, could affect function of the second protein. This strategy has been successful in a study of the homologous active sites of CR1 (Krych et. al. (1991) *Proc. Natl. Acad. Sci. USA* 88: 4353.

Three classes of mutations are presented. One class utilizes substitutions of short amino acid sequence from homologous regions of human C2 (Bmut 1–25, 30 and 34), a homologous protein not known to interact with C3b. A second class utilizes substitutions of short amino acid sequence from homologous regions of human CR3 (Bmut31 and 35), a protein which interacts with a different proteolytic fragment of C3. A third class utilizes substitutions shown to affect the activity of C2 (Bmut 26–28) or of CR3 (BMut29).

As Table 1 shows, it is possible to weaken or destroy cell lysis activity by altering amino acids in either the SCR domain (Bmut9), or in the von Willibrand Factor domain (Bmut.26,27,28,29,30,34,35). It is also possible to strengthen lysis activity (Bmut3l), a substitution within the von Willibrand Factor domain derived from of a homologous region of CR3.

These results indicate that by manipulation of the amino acids in Factor B, the capacity for complement activity can be altered. Similar alterations may be made to additional regions of Factor B.

Table 1 shows the Factor B mutations. Bmut 1–25 are SCR substitutions based on homologous regions of C2, Bmut 26–30, 34 are vWF substitutions based on homologous regions of C2, and Bmut 31, 35 are vWF substitutions based on homologous regions of Mac-1 (CR3). FIGS. 2A–I, 3A–B, 4, and 5A–B show the corresponding location of the substitutions within the sequences. The cell lysis activity of modified Factor B is compared with the unmodified Factor B standard (A14D+) which is designated a Z value of 100% or (++). A Z value between 5 to 50% of the standard is given a single (+), (++) indicates a Z value between 51–120% and (+++) indicates an activity above 120%. A (−) value indicates a Z value less than 5% of the standard. A Z value within 20% of that of A14D+, that is, between 80–120%, is not considered to be significantly different from the unmodified standard in activity.

TABLE 1

Factor B MUTATIONS
Numbering convention of Mole et al. (1984) J. Biol. Chem. 259: 3407.

| Designation | Description | | Cell Lysis Activity | Z/Z of std. × 100 (%) |
|---|---|---|---|---|
| A14D+ | Recombinant Factor B (Example 1) | | ++ | 100 |
| Bmut 1 | 13–20: | SLEGVEIK (SEQ ID NO:4) → PQNVNIS (SEQ ID NO:5) | ++ | 109 |
| Bmut 2 | 23–29: | SFRLLQE (SEQ ID NO:6) → TFTLSHG (SEQ ID NO:7) | | |
| Bmut 3 | 31–36: | QALEYV (SEQ ID NO:8) → SLLTYS (SEQ ID NO:9) | ++ | 89 |
| Bmut 4 | 39–44: | SGFYPY (SEQ ID NO:10) → QGLYPS (SEQ ID NO:11) | ++ | 85 |
| Bmut 5 | 46–50: | VQTRT (SEQ ID NO:12) → ASRL (SEQ ID NO:13) | ++ | 105 |
| Bmut 6 | 52–56: | RSTGS (SEQ ID NO:14) → KSSGQ (SEQ ID NO:15) | ++ | 93 |
| Bmut 7 | 58–65: | STLKTQDQ (SEQ ID NO:16) → QTPGATRS (SEQ ID NO:17) | | |
| Bmut 8 | 66–72: | KTVRKAE (SEQ ID NO:18) → RSLSKAV (SEQ ID NO:19) | ++ | 107 |
| Bmut 9 | 74–77: | RAIH (SEQ ID NO:20) → KPVR (SEQ ID NO:21) | + | 18 |
| Bmut 10 | 80–84: | RPHD (SEQ ID NO:22) → APVS (SEQ ID NO:23) | ++ | 123 |
| Bmut 11 | 88–95: | EYWPRSPY (SEQ ID NO:24) → IYTPRLGS (SEQ ID NO:25) | | |
| Bmut 12 | 97–105: | NVSDEISHFH (SEQ ID NO:26) → PVGGNVSFE (SEQ ID NO:27) | | |
| Bmut 13 | 107–112: | YDGYT (SEQ ID NO:28) → EDGFI (SEQ ID NO:29) | | |
| Bmut 14 | 116–119: | ANRT (SEQ ID NO:30) → PVRQ (SEQ ID NO:31) | ++ | 93 |
| Bmut 15 | 121–125: | QVNGR (SEQ ID NO:32) → RPNGM (SEQ ID NO:33) | | |
| Bmut 16 | 127–132: | SGQTAI (SEQ ID NO:34) → DGETAV (SEQ ID NO:35) | | |
| Bmut 17 | 139–142: | YCS → HCP | | |
| Bmut 18 | 146–152: | PIGTRKV (SEQ ID NO:36) → SLGAVRT (SEQ ID NO:37) | | |
| Bmut 19 | 154–159: | SQYRLE (SEQ ID NO:38) → FRFGHG (SEQ ID NO:39) | | |
| Bmut 20 | 161–165: | SVTYH (SEQ ID NO:40) → KVRYR (SEQ ID NO:41) | | |
| Bmut 21 | 168–173: | RGLTLR (SEQ ID NO:42) → SNLVLT (SEQ ID NO:43) | | |
| Bmut 22 | 176–179: | QRRT (SEQ ID NO:44) → SERE(SEQ ID NO:45) | ++ | 89 |
| Bmut 23 | 182–185: | EGGS (SEQ ID NO:46) → GNGV (SEQ ID NO:47) | | |
| Bmut 24 | 192–198: | SCQDSFM (SEQ ID NO:48) → ICRQPYS (SEQ ID NO:49) | ++ | 67 |
| Bmut 25 | 210–207: | TPQEVAE (SEQ ID NO:50) → FPEDVAP (SEQ ID NO:51) | [+] | 37 |
| Bmut 26 | 251: | D → L | + | 19 |
| Bmut 27 | 252: | G → C | + | 38 |
| Bmut 28 | 255: | S → A | − | 2 |
| Bmut 29 | 251: | D → A | − | 0* |
| Bmut 30 | 252–260: | GSDSIGASN (SEQ ID NO:52) → CSQSVSEND (SEQ ID NO:5) | + | 8 |
| Bmut 31 | 254–260: | DSIGASN (SEQ ID NO:4) → GSIIPHD (SEQ ID NO:55) | +++ | 180 |
| Bmut 34 | 366–367: | LH → KS | + | 17 |
| Bmut 35 | 366–370: | LHNMG (SEQ ID NO:56) → EKF | − | 3 |

*Not detected.

SEQUENCE LISTING (1) GENERAL INFORMATION:

(iii) NUMBER OF SEQUENCES: 62

(2) INFORMATION FOR SEQ ID NO:1:

(i) SEQUENCE CHARACTERISTICS:
        (A) LENGTH: 2483 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM:  Homo Sapiens (ix) FEATURE:
        (A) NAME/KEY: misc_feature
        (B) LOCATION: 116..2407
        (D) OTHER INFORMATION: /note= "Product = Human Factor B"

(xi) SEQUENCE DESCRIPTION: SEQ ID NO:1:

| | | | | | |
|---|---|---|---|---|---|
| TGACCAGGTC | TAGGTCTGGA | GTTTCAGCTT | GGACACTGAG | CCAAGCAGAC | AAGCAAAGCA    60 |
| AGCCAGGACA | CACCATCCTG | CCCCAGGCCC | AGCTTCTCTC | CTGCCTTCCA | ACGCCATGGG   120 |
| GAGCAATCTC | AGCCCCCAAC | TCTGCCTGAT | GCCCTTTATC | TTGGGCCTCT | TGTCTGGAGG   180 |
| TGTGACCACC | ACTCCATGGT | CTTTGGCCCA | GCCCCAGGGA | TCCTGCTCTC | TGGAGGGGGT   240 |
| AGAGATCAAA | GGCGGCTCCT | TCCGACTTCT | CCAAGAGGGC | CAGGCACTGG | AGTACGTGTG   300 |
| TCCTTCTGGC | TTCTACCCGT | ACCCTGTGCA | GACACGTACC | TGCAGATCTA | CGGGGTCCTG   360 |
| GAGCACCCTG | AAGACTCAAG | ACCAAAAGAC | TGTCAGGAAG | GCAGAGTGCA | GAGCAATCCA   420 |
| CTGTCCAAGA | CCACACGACT | TCGAGAACGG | GGAATACTGG | CCCCGGTCTC | CCTACTACAA   480 |
| TGTGAGTGAT | GAGATCTCTT | TCCACTGCTA | TGACGGTTAC | ACTCTCCGGG | GCTCTGCCAA   540 |
| TCGCACCTGC | CAAGTGAATG | GCCGGTGGAG | TGGGCAGACA | GCGATCTGTG | ACAACGGAGC   600 |
| GGGGTACTGC | TCCAACCCGG | GCATCCCCAT | TGGCACAAGG | AAGGTGGGCA | GCCAGTACCG   660 |
| CCTTGAAGAC | AGCGTCACCT | ACCACTGCAG | CCGGGGGCTT | ACCCTGCGTG | GCTCCCAGCG   720 |
| GCGAACGTGT | CAGGAAGGTG | GCTCTTGGAG | CGGGACGGAG | CCTTCCTGCC | AAGACTCCTT   780 |
| CATGTATGAC | ACCCCTCAAG | AGGTGGCCGA | AGCTTTCCTG | TCTTCCCTGA | CAGAGACCAT   840 |
| AGAAGGAGTC | GATGCTGAGG | ATGGGCACGG | CCCAGGGGAA | CAACAGAAGC | GGAAGATCGT   900 |
| CCTGGACCCT | TCAGGCTCCA | TGAACATCTA | CCTGGTGCTA | GATGGATCAG | ACAGCATTGG   960 |
| GGCCAGCAAC | TTCACAGGAG | CCAAAAAGTG | TCTAGTCAAC | TTAATTGAGA | AGGTGGCAAG  1020 |
| TTATGGTGTG | AAGCCAAGAT | ATGGTCTAGT | GACATATGCC | ACATACCCCA | AAATTTGGGT  1080 |
| CAAAGTGTCT | GAAGCAGACA | GCAGTAATGC | AGACTGGGTC | ACGAAGCAGC | TCAATGAAAT  1140 |
| CAATTATGAA | GACCACAAGT | TGAAGTCAGG | GACTAACACC | AAGAAGGCCC | TCCAGGCAGT  1200 |
| GTACAGCATG | ATGAGCTGGC | CAGATGACGT | CCCTCCTGAA | GGCTGGAACC | GCACCCGCCA  1260 |
| TGTCATCATC | CTCATGACTG | ATGGATTGCA | CAACATGGGC | GGGGACCCAA | TTACTGTCAT  1320 |
| TGATGAGATC | CGGGACTTGC | TATACATTGG | CAAGGATCGC | AAAAACCCAA | GGGAGGATTA  1380 |
| TCTGGATGTC | TATGTGTTTG | GGGTCGGGCC | TTTGGTGAAC | CAAGTGAACA | TCAATGCTTT  1440 |

-continued

```
GGCTTCCAAG AAAGACAATG AGCAACATGT GTTCAAAGTC AAGGATATGG AAAACCTGGA    1500

AGATGTTTTC TACCAAATGA TCGATGAAAG CCAGTCTCTG AGTCTCTGTG GCATGGTTTG    1560

GGAACACAGG AAGGGTACCG ATTACCACAA GCAACCATGG CAGGCCAAGA TCTCAGTCAT    1620

TCGCCCTTCA AAGGGACACG AGAGCTGTAT GGGGGCTGTG GTGTCTGAGT ACTTTGTGCT    1680

GACAGCAGCA CATTGTTTCA CTGTGGATGA CAAGGAACAC TCAATCAAGG TCAGCGTAGG    1740

AGGGGAGAAG CGGGACCTGG AGATAGAAGT AGTCCTATTT CACCCCAACT ACAACATTAA    1800

TGGGAAAAAA GAAGCAGGAA TTCCTGAATT TTATGACTAT GACGTTGCCC TGATCAAGCT    1860

CAAGAATAAG CTGAAATATG CCAGACTAT CAGGCCCATT TGTCTCCCCT GCACCGAGGG    1920

AACAACTCGA GCTTTGAGGC TTCCTCCAAC TACCACTTGC CAGCAACAAA GGAAGAGCT    1980

GCTCCCTGCA CAGGATATCA AAGCTCTGTT TGTGTCTGAG GAGGAGAAAA AGCTGACTCG    2040

GAAGGAGGTC TACATCAAGA ATGGGGATAA GAAAGGCAGC TGTGAGAGAG ATGCTCAATA    2100

TGCCCCAGGC TATGACAAAG TCAAGGACAT CTCAGAGGTG GTCACCCCTC GGTTCCTTTG    2160

TACTGGAGGA GTGAGTCCCT ATGCTGACCC CAATACTTGC AGAGGTGATT CTGGCGGCCC    2220

CTTGATAGTT CACAAGAGAA GTCGTTTCAT TCAAGTTGGT GTAATCAGCT GGGGAGTAGT    2280

GGATGTCTGC AAAAACCAGA AGCGGCAAAA GCAGGTACCT GCTCACGCCC GAGACTTTCA    2340

CATCAACCTC TTTCAAGTGC TGCCCTGGCT GAAGGAGAAA CTCCAAGATG AGGATTTGGG    2400

TTTTCTATAA GGGGTTTCCT GCTGGACAGG GGCGTGGGAT TGAATTAAAA CAGCTGCGAC    2460

AACAAAAAAA AAAAAAAAA AAA                                             2483
```

(2) INFORMATION FOR SEQ ID NO:2:

(i) SEQUENCE CHARACTERISTICS:
        (A) LENGTH: 764 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:2:

```
Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Gln
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160
```

-continued

```
Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Thr Cys Gln Glu Gly
            195                 200                 205

Gly Ser Trp Ser Gly Thr Glu Pro Ser Cys Gln Asp Ser Phe Met Tyr
            210                 215                 220

Asp Thr Pro Gln Glu Val Ala Glu Ala Phe Leu Ser Ser Leu Thr Glu
225                 230                 235                 240

Thr Ile Glu Gly Val Asp Ala Asp Gly His Gly Pro Gly Glu Gln
                245                 250                 255

Gln Lys Arg Lys Ile Val Leu Asp Pro Ser Gly Ser Met Asn Ile Tyr
            260                 265                 270

Leu Val Leu Asp Gly Ser Asp Ser Ile Gly Ala Ser Asn Phe Thr Gly
            275                 280                 285

Ala Lys Lys Cys Leu Val Asn Leu Ile Glu Lys Val Ala Ser Tyr Gly
290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
            355                 360                 365

Pro Asp Asp Val Pro Pro Glu Gly Trp Asn Arg Thr Arg His Val Ile
370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
            435                 440                 445

Glu Gln His Val Phe Lys Val Lys Asp Met Glu Asn Leu Glu Asp Val
450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
            515                 520                 525

Thr Val Asp Asp Lys Glu His Ser Ile Lys Val Ser Val Gly Gly Glu
530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590
```

```
Arg Pro Ile Cys Leu Pro Cys Thr Glu Gly Thr Thr Arg Ala Leu Arg
        595                 600                 605

Leu Pro Pro Thr Thr Thr Cys Gln Gln Gln Lys Glu Glu Leu Leu Pro
610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
                660                 665                 670

Ser Glu Val Val Thr Pro Arg Phe Leu Cys Thr Gly Val Ser Pro
                675                 680                 685

Tyr Ala Asp Pro Asn Thr Cys Arg Gly Asp Ser Gly Gly Pro Leu Ile
                690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
                740                 745                 750

Lys Glu Lys Leu Gln Asp Glu Asp Leu Gly Phe Leu
                755                 760

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

GGAAGCGGAA GAGTCGCGAG TCGACCAGAC ATG                              33

(2) INFORMATION FOR SEQ ID NO:4:

(i) SEQUENCE CHARACTERISTICS:
        (A) LENGTH: 8 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:4:

Ser Leu Glu Gly Val Glu Ile Lys
1               5

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear (ii) MOLECULE TYPE: protein
```

```
       (iii) HYPOTHETICAL: NO (xi) SEQUENCE DESCRIPTION: SEQ ID NO:5:

Pro Gln Asn Val Asn Ile Ser
1               5

(2) INFORMATION FOR SEQ ID NO:6:

(i) SEQUENCE CHARACTERISTICS:
           (A) LENGTH: 7 amino acids
           (B) TYPE: amino acid
           (D) TOPOLOGY: linear (ii) MOLECULE TYPE: protein (iii) HYPOTHETICAL: NO (xi) SEQUENCE DESCRIPTION: SEQ ID NO:6:

Ser Phe Arg Leu Leu Gln Glu
1               5

(2) INFORMATION FOR SEQ ID NO:7:

(i) SEQUENCE CHARACTERISTICS:
           (A) LENGTH: 7 amino acids
           (B) TYPE: amino acid
           (D) TOPOLOGY: linear (ii) MOLECULE TYPE: protein (iii) HYPOTHETICAL: NO (xi) SEQUENCE DESCRIPTION: SEQ ID NO:7:

Thr Phe Thr Leu Ser His Gly
1               5

(2) INFORMATION FOR SEQ ID NO:8:

(i) SEQUENCE CHARACTERISTICS:
           (A) LENGTH: 6 amino acids
           (B) TYPE: amino acid
           (D) TOPOLOGY: linear (ii) MOLECULE TYPE: protein (iii) HYPOTHETICAL: NO (xi) SEQUENCE DESCRIPTION: SEQ ID NO:8:

Gln Ala Leu Glu Tyr Val
1               5

(2) INFORMATION FOR SEQ ID NO:9:

(i) SEQUENCE CHARACTERISTICS:
           (A) LENGTH: 6 amino acids
           (B) TYPE: amino acid
           (D) TOPOLOGY: linear (ii) MOLECULE TYPE: protein (iii) HYPOTHETICAL: NO (xi) SEQUENCE DESCRIPTION: SEQ ID NO:9:

Ser Leu Leu Thr Tyr Ser
1               5

(2) INFORMATION FOR SEQ ID NO:10:

(i) SEQUENCE CHARACTERISTICS:
           (A) LENGTH: 6 amino acids
```

```
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:10:

Ser Gly Phe Tyr Pro Tyr
1               5

(2) INFORMATION FOR SEQ ID NO:11:

(i) SEQUENCE CHARACTERISTICS:
        (A) LENGTH: 6 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:11:

Gln Gly Leu Tyr Pro Ser
1               5

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:12:

Val Gln Thr Arg Thr
1               5

(2) INFORMATION FOR SEQ ID NO:13:

(i) SEQUENCE CHARACTERISTICS:
        (A) LENGTH: 4 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:13:

Ala Ser Arg Leu
1

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:14:

Arg Ser Thr Gly Ser
1               5
```

(2) INFORMATION FOR SEQ ID NO:15:

(i) SEQUENCE CHARACTERISTICS:
        (A) LENGTH: 5 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:15:

Lys Ser Ser Gly Gln
1          5

(2) INFORMATION FOR SEQ ID NO:16:

(i) SEQUENCE CHARACTERISTICS:
        (A) LENGTH: 8 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:16:

Ser Thr Leu Lys Thr Gln Asp Gln
1          5

(2) INFORMATION FOR SEQ ID NO:17:

(i) SEQUENCE CHARACTERISTICS:
        (A) LENGTH: 8 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:17:

Gln Thr Pro Gly Ala Thr Arg Ser
1          5

(2) INFORMATION FOR SEQ ID NO:18:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:18:

Lys Thr Val Arg Lys Ala Glu
1          5

(2) INFORMATION FOR SEQ ID NO:19:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO

```
          (xi) SEQUENCE DESCRIPTION: SEQ ID NO:19:

Arg Ser Leu Ser Lys Ala Val
1               5

(2) INFORMATION FOR SEQ ID NO:20:

(i) SEQUENCE CHARACTERISTICS:
         (A) LENGTH: 4 amino acids
         (B) TYPE: amino acid
         (D) TOPOLOGY: linear (ii) MOLECULE TYPE: protein (iii) HYPOTHETICAL: NO (xi) SEQUENCE DESCRIPTION: SEQ ID NO:20:

Arg Ala Ile His
1

(2) INFORMATION FOR SEQ ID NO:21:

(i) SEQUENCE CHARACTERISTICS:
         (A) LENGTH: 4 amino acids
         (B) TYPE: amino acid
         (D) TOPOLOGY: linear (ii) MOLECULE TYPE: protein (iii) HYPOTHETICAL: NO (xi) SEQUENCE DESCRIPTION: SEQ ID NO:21:

Lys Pro Val Arg
1

(2) INFORMATION FOR SEQ ID NO:22:

(i) SEQUENCE CHARACTERISTICS:
         (A) LENGTH: 4 amino acids
         (B) TYPE: amino acid
         (D) TOPOLOGY: linear (ii) MOLECULE TYPE: protein (iii) HYPOTHETICAL: NO (xi) SEQUENCE DESCRIPTION: SEQ ID NO:22:

Arg Pro His Asp
1

(2) INFORMATION FOR SEQ ID NO:23:

(i) SEQUENCE CHARACTERISTICS:
         (A) LENGTH: 4 amino acids
         (B) TYPE: amino acid
         (D) TOPOLOGY: linear (ii) MOLECULE TYPE: protein (iii) HYPOTHETICAL: NO (xi) SEQUENCE DESCRIPTION: SEQ ID NO:23:

Ala Pro Val Ser
1

(2) INFORMATION FOR SEQ ID NO:24:

(i) SEQUENCE CHARACTERISTICS:
         (A) LENGTH: 8 amino acids
         (B) TYPE: amino acid
         (D) TOPOLOGY: linear
```

```
      (ii) MOLECULE TYPE: protein (iii) HYPOTHETICAL: NO (xi) SEQUENCE DESCRIPTION: SEQ ID NO:24:

Glu Tyr Trp Pro Arg Ser Pro Tyr
1               5

(2) INFORMATION FOR SEQ ID NO:25:

(i) SEQUENCE CHARACTERISTICS:
          (A) LENGTH: 8 amino acids
          (B) TYPE: amino acid
          (D) TOPOLOGY: linear (ii) MOLECULE TYPE: protein (iii) HYPOTHETICAL: NO (xi) SEQUENCE DESCRIPTION: SEQ ID NO:25:

Ile Tyr Thr Pro Arg Leu Gly Ser
1               5

(2) INFORMATION FOR SEQ ID NO:26:

(i) SEQUENCE CHARACTERISTICS:
          (A) LENGTH: 9 amino acids
          (B) TYPE: amino acid
          (D) TOPOLOGY: linear (ii) MOLECULE TYPE: protein (iii) HYPOTHETICAL: NO (xi) SEQUENCE DESCRIPTION: SEQ ID NO:26:

Asn Val Ser Asp Glu Ile Ser Phe His
1               5

(2) INFORMATION FOR SEQ ID NO:27:

(i) SEQUENCE CHARACTERISTICS:
          (A) LENGTH: 9 amino acids
          (B) TYPE: amino acid
          (D) TOPOLOGY: linear (ii) MOLECULE TYPE: protein (iii) HYPOTHETICAL: NO (xi) SEQUENCE DESCRIPTION: SEQ ID NO:27:

Pro Val Gly Gly Asn Val Ser Phe Glu
1               5

(2) INFORMATION FOR SEQ ID NO:28:

(i) SEQUENCE CHARACTERISTICS:
          (A) LENGTH: 5 amino acids
          (B) TYPE: amino acid
          (D) TOPOLOGY: linear (ii) MOLECULE TYPE: protein (iii) HYPOTHETICAL: NO (xi) SEQUENCE DESCRIPTION: SEQ ID NO:28:

Tyr Asp Gly Tyr Thr
1               5

(2) INFORMATION FOR SEQ ID NO:29:
```

```
      (i) SEQUENCE CHARACTERISTICS:
          (A) LENGTH: 5 amino acids
          (B) TYPE: amino acid
          (D) TOPOLOGY: linear (ii) MOLECULE TYPE: protein (iii) HYPOTHETICAL: NO (xi) SEQUENCE DESCRIPTION: SEQ ID NO:29:

Glu Asp Gly Phe Ile
1               5

(2) INFORMATION FOR SEQ ID NO:30:

(i) SEQUENCE CHARACTERISTICS:
          (A) LENGTH: 4 amino acids
          (B) TYPE: amino acid
          (D) TOPOLOGY: linear (ii) MOLECULE TYPE: protein (iii) HYPOTHETICAL: NO (xi) SEQUENCE DESCRIPTION: SEQ ID NO:30:

Ala Asn Arg Thr
1

(2) INFORMATION FOR SEQ ID NO:31:

(i) SEQUENCE CHARACTERISTICS:
          (A) LENGTH: 4 amino acids
          (B) TYPE: amino acid
          (D) TOPOLOGY: linear (ii) MOLECULE TYPE: protein (iii) HYPOTHETICAL: NO (xi) SEQUENCE DESCRIPTION: SEQ ID NO:31:

Pro Val Arg Gln
1

(2) INFORMATION FOR SEQ ID NO:32:

(i) SEQUENCE CHARACTERISTICS:
          (A) LENGTH: 5 amino acids
          (B) TYPE: amino acid
          (D) TOPOLOGY: linear (ii) MOLECULE TYPE: protein (iii) HYPOTHETICAL: NO (xi) SEQUENCE DESCRIPTION: SEQ ID NO:32:

Gln Val Asn Gly Arg
1               5

(2) INFORMATION FOR SEQ ID NO:33:

(i) SEQUENCE CHARACTERISTICS:
          (A) LENGTH: 5 amino acids
          (B) TYPE: amino acid
          (D) TOPOLOGY: linear (ii) MOLECULE TYPE: protein (iii) HYPOTHETICAL: NO (xi) SEQUENCE DESCRIPTION: SEQ ID NO:33:
```

```
Arg Pro Asn Gly Met
1               5
```

(2) INFORMATION FOR SEQ ID NO:34:

(i) SEQUENCE CHARACTERISTICS:
        (A) LENGTH: 6 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:34:

```
Ser Gly Gln Thr Ala Ile
1               5
```

(2) INFORMATION FOR SEQ ID NO:35:

(i) SEQUENCE CHARACTERISTICS:
        (A) LENGTH: 6 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:35:

```
Asp Gly Glu Thr Ala Val
1               5
```

(2) INFORMATION FOR SEQ ID NO:36:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:36:

```
Pro Ile Gly Thr Arg Lys Val
1               5
```

(2) INFORMATION FOR SEQ ID NO:37:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:37:

```
Ser Leu Gly Ala Val Arg Thr
1               5
```

(2) INFORMATION FOR SEQ ID NO:38:

(i) SEQUENCE CHARACTERISTICS:
        (A) LENGTH: 6 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:38:

Ser Gln Tyr Arg Leu Glu
1               5

(2) INFORMATION FOR SEQ ID NO:39:

(i) SEQUENCE CHARACTERISTICS:
            (A) LENGTH: 6 amino acids
            (B) TYPE: amino acid
            (D) TOPOLOGY: linear (ii) MOLECULE TYPE: protein (iii) HYPOTHETICAL: NO (xi) SEQUENCE DESCRIPTION: SEQ ID NO:39:

Phe Arg Phe Gly His Gly
1               5

(2) INFORMATION FOR SEQ ID NO:40:

(i) SEQUENCE CHARACTERISTICS:
            (A) LENGTH: 5 amino acids
            (B) TYPE: amino acid
            (D) TOPOLOGY: linear (ii) MOLECULE TYPE: protein (iii) HYPOTHETICAL: NO (xi) SEQUENCE DESCRIPTION: SEQ ID NO:40:

Ser Val Thr Tyr His
1               5

(2) INFORMATION FOR SEQ ID NO:41:

(i) SEQUENCE CHARACTERISTICS:
            (A) LENGTH: 5 amino acids
            (B) TYPE: amino acid
            (D) TOPOLOGY: linear (ii) MOLECULE TYPE: protein (iii) HYPOTHETICAL: NO (xi) SEQUENCE DESCRIPTION: SEQ ID NO:41:

Lys Val Arg Tyr Arg
1               5

(2) INFORMATION FOR SEQ ID NO:42:

(i) SEQUENCE CHARACTERISTICS:
            (A) LENGTH: 6 amino acids
            (B) TYPE: amino acid
            (D) TOPOLOGY: linear (ii) MOLECULE TYPE: protein (iii) HYPOTHETICAL: NO (xi) SEQUENCE DESCRIPTION: SEQ ID NO:42:

Arg Gly Leu Thr Leu Arg
1               5

(2) INFORMATION FOR SEQ ID NO:43:

(i) SEQUENCE CHARACTERISTICS:

(A) LENGTH: 6 amino acids
            (B) TYPE: amino acid
            (D) TOPOLOGY: linear (ii) MOLECULE TYPE: protein (iii) HYPOTHETICAL: NO (xi) SEQUENCE DESCRIPTION: SEQ ID NO:43:

Ser Asn Leu Val Leu Thr
1               5

(2) INFORMATION FOR SEQ ID NO:44:

(i) SEQUENCE CHARACTERISTICS:
            (A) LENGTH: 4 amino acids
            (B) TYPE: amino acid
            (D) TOPOLOGY: linear (ii) MOLECULE TYPE: protein (iii) HYPOTHETICAL: NO (xi) SEQUENCE DESCRIPTION: SEQ ID NO:44:

Gln Arg Arg Thr
1

(2) INFORMATION FOR SEQ ID NO:45:

(i) SEQUENCE CHARACTERISTICS:
            (A) LENGTH: 4 amino acids
            (B) TYPE: amino acid
            (D) TOPOLOGY: linear (ii) MOLECULE TYPE: protein (iii) HYPOTHETICAL: NO (xi) SEQUENCE DESCRIPTION: SEQ ID NO:45:

Ser Glu Arg Glu
1

(2) INFORMATION FOR SEQ ID NO:46:

(i) SEQUENCE CHARACTERISTICS:
            (A) LENGTH: 4 amino acids
            (B) TYPE: amino acid
            (D) TOPOLOGY: linear (ii) MOLECULE TYPE: protein (iii) HYPOTHETICAL: NO (xi) SEQUENCE DESCRIPTION: SEQ ID NO:46:

Glu Gly Gly Ser
1

(2) INFORMATION FOR SEQ ID NO:47:

(i) SEQUENCE CHARACTERISTICS:
            (A) LENGTH: 4 amino acids
            (B) TYPE: amino acid
            (D) TOPOLOGY: linear (ii) MOLECULE TYPE: protein (iii) HYPOTHETICAL: NO (xi) SEQUENCE DESCRIPTION: SEQ ID NO:47:

Gly Asn Gly Val
1

(2) INFORMATION FOR SEQ ID NO:48:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:48:

```
Ser Cys Gln Asp Ser Phe Met
1               5
```

(2) INFORMATION FOR SEQ ID NO:49:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:49:

```
Ile Cys Arg Gln Pro Tyr Ser
1               5
```

(2) INFORMATION FOR SEQ ID NO:50:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:50:

```
Thr Pro Gln Glu Val Ala Glu
1               5
```

(2) INFORMATION FOR SEQ ID NO:51:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:51:

```
Phe Pro Glu Asp Val Ala Pro
1               5
```

(2) INFORMATION FOR SEQ ID NO:52:

(i) SEQUENCE CHARACTERISTICS:
        (A) LENGTH: 9 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:52:

Gly Ser Asp Ser Ile Gly Ala Ser Asn
1               5

(2) INFORMATION FOR SEQ ID NO:53:

(i) SEQUENCE CHARACTERISTICS:
         (A) LENGTH: 9 amino acids
         (B) TYPE: amino acid
         (D) TOPOLOGY: linear (ii) MOLECULE TYPE: protein (iii) HYPOTHETICAL: NO (xi) SEQUENCE DESCRIPTION: SEQ ID NO:53:

Cys Ser Gln Ser Val Ser Glu Asn Asp
1               5

(2) INFORMATION FOR SEQ ID NO:54:

(i) SEQUENCE CHARACTERISTICS:
         (A) LENGTH: 7 amino acids
         (B) TYPE: amino acid
         (D) TOPOLOGY: linear (ii) MOLECULE TYPE: protein (iii) HYPOTHETICAL: NO (xi) SEQUENCE DESCRIPTION: SEQ ID NO:54:

Asp Ser Ile Gly Ala Ser Asn
1               5

(2) INFORMATION FOR SEQ ID NO:55:

(i) SEQUENCE CHARACTERISTICS:
         (A) LENGTH: 7 amino acids
         (B) TYPE: amino acid
         (D) TOPOLOGY: linear (ii) MOLECULE TYPE: protein (iii) HYPOTHETICAL: NO (xi) SEQUENCE DESCRIPTION: SEQ ID NO:55:

Gly Ser Ile Ile Pro His Asp
1               5

(2) INFORMATION FOR SEQ ID NO:56:

(i) SEQUENCE CHARACTERISTICS:
         (A) LENGTH: 5 amino acids
         (B) TYPE: amino acid
         (D) TOPOLOGY: linear (ii) MOLECULE TYPE: protein (iii) HYPOTHETICAL: NO (xi) SEQUENCE DESCRIPTION: SEQ ID NO:56:

Leu His Asn Met Gly
1               5

(2) INFORMATION FOR SEQ ID NO:57:

(i) SEQUENCE CHARACTERISTICS:
         (A) LENGTH: 265 amino acids
         (B) TYPE: amino acid -continued (D) TOPOLOGY: linear (ii) MOLECULE TYPE: protein (iii) HYPOTHETICAL: NO (xi) SEQUENCE DESCRIPTION: SEQ ID NO:57:

```
Thr Pro Trp Ser Leu Ala Gln Pro Gln Gly Ser Cys Ser Leu Glu Gly
 1               5                  10                  15

Val Glu Ile Lys Gly Gly Ser Phe Arg Leu Gln Glu Gly Gln Ala
            20                  25                  30

Leu Glu Tyr Val Cys Pro Ser Gly Phe Tyr Pro Tyr Pro Val Gln Thr
            35                  40                  45

Arg Thr Cys Arg Ser Thr Gly Ser Trp Ser Thr Leu Lys Thr Gln Asp
 50                  55                  60

Gln Lys Thr Val Arg Lys Ala Glu Cys Arg Ala Ile His Cys Pro Arg
 65                  70                  75                  80

Pro His Asp Phe Glu Asn Gly Glu Tyr Trp Pro Arg Ser Pro Tyr Tyr
                85                  90                  95

Asn Val Ser Asp Glu Ile Ser Phe His Cys Tyr Asp Gly Tyr Thr Leu
                100                 105                 110

Arg Gly Ser Ala Asn Arg Thr Cys Gln Val Asn Gly Arg Trp Ser Gly
            115                 120                 125

Gln Thr Ala Ile Cys Asp Asn Gly Ala Gly Tyr Cys Ser Asn Pro Gly
130                 135                 140

Ile Pro Ile Gly Thr Arg Lys Val Gly Ser Gln Tyr Arg Leu Glu Asp
145                 150                 155                 160

Ser Val Thr Tyr His Cys Ser Arg Gly Leu Thr Leu Arg Gly Ser Gln
                165                 170                 175

Arg Arg Thr Cys Gln Glu Gly Gly Ser Trp Ser Gly Thr Glu Pro Ser
            180                 185                 190

Cys Gln Asp Ser Phe Met Tyr Asp Thr Pro Gln Glu Val Ala Glu Ala
            195                 200                 205

Phe Leu Ser Ser Leu Thr Glu Thr Ile Glu Gly Val Asp Ala Glu Asp
210                 215                 220

Gly His Gly Pro Gly Glu Gln Gln Lys Arg Lys Ile Val Leu Asp Pro
225                 230                 235                 240

Ser Gly Ser Met Asn Ile Tyr Leu Val Leu Asp Gly Ser Asp Ser Ile
                245                 250                 255

Gly Ala Ser Asn Phe Thr Gly Ala Lys
                260                 265
```

(2) INFORMATION FOR SEQ ID NO:58:

(i) SEQUENCE CHARACTERISTICS:
        (A) LENGTH: 274 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:58:

```
Met Gly Pro Leu Met Val Leu Phe Cys Leu Leu Phe Leu Tyr Pro Gly
 1               5                  10                  15

Leu Ala Asp Ser Ala Pro Ser Cys Pro Gln Asn Val Asn Ile Ser Gly
            20                  25                  30

Gly Thr Phe Thr Leu Ser His Gly Trp Ala Pro Gly Ser Leu Leu Thr
```

```
                35                  40                  45
Tyr Ser Cys Pro Gln Gly Leu Tyr Pro Ser Pro Ala Ser Arg Leu Cys
    50                  55                  60

Lys Ser Ser Gly Gln Trp Gln Thr Pro Gly Ala Thr Arg Ser Leu Ser
65                  70                  75                  80

Lys Ala Val Cys Lys Pro Val Arg Cys Pro Ala Pro Val Ser Phe Glu
                85                  90                  95

Asn Gly Ile Tyr Thr Pro Arg Leu Gly Ser Tyr Pro Val Gly Gly Asn
            100                 105                 110

Val Ser Phe Glu Cys Glu Asp Gly Phe Ile Leu Arg Gly Ser Pro Val
        115                 120                 125

Arg Gln Cys Arg Pro Asn Gly Met Trp Asp Gly Glu Thr Ala Val Cys
    130                 135                 140

Asp Asn Gly Ala Gly His Cys Pro Asn Pro Gly Ile Ser Leu Gly Ala
145                 150                 155                 160

Val Arg Thr Gly Phe Arg Phe Gly His Gly Asp Lys Val Arg Tyr Arg
                165                 170                 175

Cys Ser Ser Asn Leu Val Leu Thr Gly Ser Ser Glu Arg Glu Cys Gln
            180                 185                 190

Gly Asn Gly Val Trp Ser Gly Thr Glu Pro Ile Cys Arg Gln Pro Tyr
        195                 200                 205

Ser Tyr Asp Phe Pro Glu Asp Val Ala Pro Ala Leu Gly Thr Ser Phe
    210                 215                 220

Ser His Met Leu Gly Ala Thr Asn Pro Thr Gln Lys Thr Lys Glu Ser
225                 230                 235                 240

Leu Gly Arg Lys Ile Gln Ile Gln Arg Ser Gly His Leu Asn Leu Tyr
                245                 250                 255

Leu Leu Leu Asp Cys Ser Gln Ser Val Ser Glu Asn Asp Phe Leu Ile
            260                 265                 270

Phe Lys (2) INFORMATION FOR SEQ ID NO:59:

(i) SEQUENCE CHARACTERISTICS:
        (A) LENGTH: 207 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:59:

Asp Pro Ser Gly Ser Met Asn Ile Tyr Leu Val Leu Asp Gly Ser Asp
1               5                   10                  15

Ser Ile Gly Ala Ser Asn Phe Thr Gly Ala Lys Lys Cys Leu Val Asn
                20                  25                  30

Leu Ile Glu Lys Val Ala Ser Tyr Gly Val Lys Pro Arg Tyr Gly Leu
            35                  40                  45

Val Thr Tyr Ala Thr Tyr Pro Lys Ile Trp Val Lys Val Ser Glu Ala
        50                  55                  60

Asp Ser Ser Asn Ala Asp Trp Val Thr Lys Gln Leu Asn Glu Ile Asn
65                  70                  75                  80

Tyr Glu Asp His Lys Leu Lys Ser Gly Thr Asn Thr Lys Lys Ala Leu
                85                  90                  95

Gln Ala Val Tyr Ser Met Met Ser Trp Pro Asp Asp Val Pro Pro Glu
            100                 105                 110
```

```
Gly Trp Asn Arg Thr Arg His Val Ile Ile Leu Met Thr Asp Gly Leu
            115                 120                 125

His Asn Met Gly Gly Asp Pro Ile Thr Val Ile Asp Glu Ile Arg Asp
    130                 135                 140

Leu Leu Tyr Ile Gly Lys Asp Arg Lys Asn Pro Arg Glu Asp Tyr Leu
145                 150                 155                 160

Asp Val Tyr Val Phe Gly Val Gly Pro Leu Val Asn Gln Val Asn Ile
                165                 170                 175

Asn Ala Leu Ala Ser Lys Lys Asp Asn Glu Gln His Val Phe Lys Val
            180                 185                 190

Lys Asp Met Glu Asn Leu Glu Asp Val Phe Tyr Gln Met Ile Asp
            195                 200                 205
```

(2) INFORMATION FOR SEQ ID NO:60:

(i) SEQUENCE CHARACTERISTICS:
        (A) LENGTH: 207 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:60:

```
Gln Arg Ser Gly His Leu Asn Leu Tyr Leu Leu Asp Cys Ser Gln
1               5                   10                  15

Ser Val Ser Glu Asn Asp Phe Leu Ile Phe Lys Glu Ser Ala Ser Leu
            20                  25                  30

Met Val Asp Arg Ile Phe Ser Phe Glu Ile Asn Val Ser Val Ala Ile
            35                  40                  45

Ile Thr Phe Ala Ser Glu Pro Lys Val Leu Met Ser Val Leu Asn Asp
50                  55                  60

Asn Ser Arg Asp Met Thr Glu Val Ile Ser Ser Leu Glu Asn Ala Asn
65                  70                  75                  80

Tyr Lys Asp His Glu Asn Gly Thr Gly Thr Asn Thr Tyr Ala Ala Leu
            85                  90                  95

Asn Ser Val Tyr Leu Met Met Asn Asn Gln Met Arg Leu Leu Gly Met
            100                 105                 110

Glu Thr Met Ala Trp Gln Glu Ile Arg His Ala Ile Ile Leu Leu Thr
            115                 120                 125

Asp Gly Lys Ser Asn Met Gly Gly Ser Pro Lys Thr Ala Val Asp His
    130                 135                 140

Ile Arg Glu Ile Leu Asn Ile Asn Gln Lys Arg Asn Asp Tyr Leu Asp
145                 150                 155                 160

Ile tyr Ala Ile Gly Val Gly Lys Leu Asp Val Asp Trp Arg Glu Leu
                165                 170                 175

Asn Glu Leu Gly Ser Lys Lys Asp Gly Glu Arg His Ala Phe Ile Leu
            180                 185                 190

Gln Asp Thr Lys Ala Leu His Gln Val Phe Glu His Met Leu Asp
            195                 200                 205
```

(2) INFORMATION FOR SEQ ID NO:61:

(i) SEQUENCE CHARACTERISTICS:
        (A) LENGTH: 187 amino acids
        (B) TYPE: amino acid
        (D) TOPOLOGY: linear -continued (ii) MOLECULE TYPE: protein (iii) HYPOTHETICAL: NO (xi) SEQUENCE DESCRIPTION: SEQ ID NO:61:

Cys Pro Gln Glu Asp Ser Asp Ile Ala Phe Leu Ile Asp Gly Ser Gly
1               5                  10                  15

Ser Ile Ile Pro His Asp Phe Arg Arg Met Lys Glu Phe Val Ser Thr
            20                  25                  30

Val Met Glu Gln Leu Lys Lys Ser Lys Thr Leu Phe Ser Leu Met Gln
        35                  40                  45

Tyr Ser Glu Glu Phe Arg Ile His Phe Thr Phe Lys Glu Phe Gln Asn
    50                  55                  60

Asn Pro Asn Pro Arg Ser Leu Val Lys Pro Ile Thr Gln Leu Leu Gly
65                  70                  75                  80

Arg Thr His Thr Ala Thr Gly Ile Arg Lys Val Val Arg Glu Leu Phe
                85                  90                  95

Asn Ile Thr Asn Gly Ala Arg Lys Asn Ala Phe Lys Ile Leu Val Val
            100                 105                 110

Ile Thr Asp Gly Glu Lys Phe Gly Asp Pro Leu Gly Tyr Glu Asp Val
        115                 120                 125

Ile Pro Glu Ala Asp Arg Glu Gly Val Ile Arg Tyr Val Ile Gly Val
    130                 135                 140

Gly Asp Ala Phe Arg Ser Glu Lys Ser Arg Gln Glu Leu Asn Thr Ile
145                 150                 155                 160

Ala Ser Lys Pro Pro Arg Asp His Val Phe Gln Val Asn Asn Phe Glu
                165                 170                 175

Ala Leu Lys Thr Ile Gln Asn Gln Leu Arg Glu
            180                 185

(2) INFORMATION FOR SEQ ID NO:62:

(i) SEQUENCE CHARACTERISTICS:
        (A) LENGTH: 187 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:62:

Cys Pro Arg Gln Glu Asp Ile Val Phe Leu Ile Asp Gly Ser Gly
1               5                  10                  15

Ser Ile Ser Ser Arg Asn Phe Ala Thr Met Met Asn Phe Val Arg Ala
            20                  25                  30

Val Ile Ser Gln Phe Gln Arg Pro Ser Thr Gln Phe Ser Leu Met Gln
        35                  40                  45

Phe Ser Asn Lys Phe Gln Thr His Phe Thr Phe Glu Glu Phe Arg Arg
    50                  55                  60

Thr Ser Asn Pro Leu Ser Leu Leu Ala Ser Val His Gln Leu Gln Gly
65                  70                  75                  80

Phe Thr Tyr Thr Ala Thr Ala Ile Gln Asn Val Val His Arg Leu Phe
                85                  90                  95

His Ala Ser Tyr Gly Ala Arg Arg Asp Ala Thr Lys Ile Leu Ile Val
            100                 105                 110

Ile Thr Asp Gly Lys Lys Glu Gly Asp Ser Leu Asp Tyr Lys Asp Val
        115                 120                 125

-continued

```
Ile Pro Met Ala Asp Ala Ala Gly Ile Ile Arg Tyr Ala Ile Gly Val
    130                 135                 140

Gly Leu Ala Phe Gln Asn Arg Asn Ser Trp Lys Glu Leu Asn Asp Ile
145             150                 155                 160

Ala Ser Lys Pro Ser Gln Glu His Ile Phe Lys Val Glu Asp Phe Asp
                165             170                 175

Ala Leu Lys Asp Ile Gln Asn Gln Leu Lys Glu
            180                 185
```

What is claimed is:

1. A nucleic acid segment encoding a Factor B analog that exhibits modified complement-mediated activity in vitro, wherein the Factor B analog consists of SEQ ID NO:2 with one or more amino acids in a short consensus repeat domain or a von Willebrand Factor domain replaced by one or more amino acids from a corresponding region of a short consensus repeat domain or a von Willebrand Factor domain of a second protein.

2. The nucleic acid segment of claim 1 wherein the modified complement-mediated activity is a change in cell lysis activity.

3. The nucleic acid segment of claim 1 wherein the second protein is selected from the group consisting of C1 r, C1 s, C2, Factor D and Factor I.

4. The nucleic acid segment of claim 1 wherein an entire short consensus repeat or von Willebrand Factor domain is replaced by a corresponding region of the second protein.

5. The nucleic acid segment of claim 1 which is of human origin.

6. The nucleic acid segment of claim 1 wherein the corresponding region of the second protein is identified by aligning the amino acid sequence of the second protein to consensus sequences of short consensus repeat or von Willebrand Factor domains.

7. The nucleic acid segment of claim 1 wherein the second protein is human C2.

8. The nucleic acid segment of claim 1 wherein the second protein is human CR3.

9. The nucleic acid segment of claim 1 wherein the activity of C2 or of CR3 is affected.

10. The nucleic acid segment of claim 1 wherein the modified complement-mediated activity is modified protein-protein interactions, modified proteolytic activity, modified recognition of substrate, inhibition of assembly, inactivation of function, modified dissociation of complexes, and modified anaphylatoxin activity.

11. A nucleic acid segment encoding a Factor B analog that exhibits modified complement-mediated activity in vitro, wherein the Factor B analog consists of SEQ ID NO:2 truncated at Arg-234 with one or more amino acids in a short consensus repeat domain or a von Willebrand Factor domain replaced by one or more amino acids from a corresponding region of a short consensus repeat domain or a von Willebrand Factor domain of a second protein.

12. A nucleic acid segment encoding a Factor B analog wherein the Factor B analog exhibits increased complement-mediated cell lysis activity over native Factor B, the Factor B analog consisting of a GSIIPHD (SEQ ID NO:55) amino acid substitution at position 279–285 of SEQ ID NO:2.

13. A nucleic acid segment encoding a Factor B analog wherein the Factor B analog is substantially inactive in complement-mediated cell lysis, the Factor B analog consisting of an alanine substitution at position 251 or 255 or both of SEQ ID NO:2.

14. A nucleic acid segment encoding a Factor B analog wherein at least one short consensus repeat domain of native human Factor B shown in SEQ ID NO:2 has been substituted with at least one short consensus repeat domain of a second complement protein.

15. A nucleic acid segment encoding a Factor B analog wherein a von Willebrand Factor domain of native Factor B shown in SEQ ID NO:2 has been substituted with a von Willebrand Factor domain of a second complement protein.

16. The nucleic acid segment of claim 15 wherein the second complement protein is C2 or CR3 (Mac-1).

17. A nucleic acid segment encoding a Factor B analog wherein a protease domain of native Factor B shown in SEQ ID NO:2 is substituted by a protease domain of C2.

18. A nucleic acid segment encoding a Factor B analog wherein the Factor B analog consists of SEQ ID NO:2 having one or more amino acid substitutions consisting of amino acids 38–45 of SEQ ID NO:2 replaced with PQNVNIS (SEQ ID NO:5);
amino acids 48–54 of SEQ ID NO:2 replaced with TFTLSHG (SEQ ID NO:7);
amino acids 56–61 of SEQ ID NO:2 replaced with SLLTYS (SEQ ID NO:9);
amino acids 64–69 of SEQ ID NO:2 replaced with QGLYPS (SEQ ID NO:11);
amino acids 71–75 of SEQ ID NO:2 replaced with ASRL (SEQ ID NO:13);
amino acids 77–81 of SEQ ID NO:2 replaced with KSSGQ (SEQ ID NO:15);
amino acids 83–90 of SEQ ID NO:2 replaced with QTPGATRS (SEQ ID NO:17);
amino acids 91–97 of SEQ ID NO:2 replaced with RSLSKAV (SEQ ID NO:19);
amino acids 99–102 of SEQ ID NO:2 replaced with KPVR (SEQ ID NO:21);
amino acids 105–109 of SEQ ID NO:2 replaced with APVS (SEQ ID NO:23);
amino acids 113–120 of SEQ ID NO:2 replaced with IYTPRLGS (SEQ ID NO:25);
amino acids 122–130 of SEQ ID NO:2 replaced with PVGGNVSFE (SEQ ID NO:27);
amino acids 132–136 of SEQ ID NO:2 replaced with EDGFI (SEQ ID NO:29);
amino acids 141–144 of SEQ ID NO:2 replaced with PVRQ (SEQ ID NO:31);
amino acids 146–150 of SEQ ID NO:2 replaced with RPNGM (SEQ ID NO:33);
amino acids 152–157 of SEQ ID NO:2 replaced with DGETAV (SEQ ID NO:35);
amino acids 164–166 of SEQ ID NO:2 replaced with HCP;
amino acids 171–177 of SEQ ID NO:2 replaced with SLGAVRT (SEQ ID NO:37);
amino acids 179–184 of SEQ ID NO:2 replaced with FRFGHG (SEQ ID NO:39);

amino acids 186–190 of SEQ ID NO:2 replaced with KVRYR (SEQ ID NO:41);
amino acids 193–198 of SEQ ID NO:2 replaced with SNLVLT (SEQ ID NO:43);
amino acids 201–204 of SEQ ID NO:2 replaced with SERE (SEQ ID NO:45);
amino acids 207–210 of SEQ ID NO:2 replaced with GNGV (SEQ ID NO:47);
amino acids 217–223 of SEQ ID NO:2 replaced with ICRQPYS (SEQ ID NO:49);
amino acids 235–242 of SEQ ID NO:2 replaced with FPEDVAP (SEQ ID NO:51);
amino acid 276 of SEQ ID NO:2 replaced with L;
amino acid 277 of SEQ ID NO:2 replaced with C;
amino acid 280 of SEQ ID NO:2 replaced with A;
amino acid 276 of SEQ ID NO:2 replaced with A;
amino acids 277–285 of SEQ ID NO:2 replaced with CSQSVSEND (SEQ ID NO:53);
amino acids 279–285 of SEQ ID NO:2 replaced with GSIIPHD (SEQ ID NO:55);
amino acids 391–392 of SEQ ID NO:2 replaced with KS; and
amino acids 391–395 of SEQ ID NO:2 replaced with EKG.

19. The nucleic acid segment of claim 18 consisting of SEQ ID NO:2 having one of the amino acid substitutions.

20. A method of producing a Factor B analog that exhibits modified complement-mediated activity in vitro, wherein the Factor B analog consists of SEQ ID NO:2 with one or more amino acids in a short consensus repeat domain replaced by one or more amino acids from a corresponding region of a short consensus repeat domain of a second protein, the method comprising
 a) growing cells transfected with a nucleotide sequence encoding the Factor B analog; and
 b) isolating the Factor B analog from the supernatant or cell lysate.

21. A nucleic acid segment encoding a Factor B analog wherein the Factor B analog that exhibits modified complement-mediated activity in vitro relative to native Factor B, wherein the Factor B analog consists of SEQ ID NO:2 with one or more amino acids in a short consensus repeat domain or a von Willebrand Factor domain replaced by one or more amino acids from a corresponding region of a short consensus repeat domain or a von Willebrand Factor domain of a second protein.

22. A nucleic acid segment encoding a Factor B analog wherein the Factor B analog exhibits modified complement-mediated activity in vitro, wherein the Factor B analog consists of SEQ ID NO:2 with one or more regions in a short consensus repeat domain or a von Willebrand Factor domain replaced by one or more corresponding regions of a short consensus repeat domain or a von Willebrand Factor domain of a second protein.

* * * * *